(12) United States Patent
Yatsui et al.

(10) Patent No.: US 7,196,518 B2
(45) Date of Patent: Mar. 27, 2007

(54) MAGNETIC RESONANCE METHOD WHICH AUTOMATICALLY FORMS WATER/FAT SEPARATED IMAGES WITH DIFFERENT ECHO TIMES AND DETERMINES THAT PROPER PHASE UNWRAPPING HAS BEEN UTILIZED

(75) Inventors: Yumiko Yatsui, Abiko (JP); Tetsuhiko Takahashi, Soka (JP)

(73) Assignee: Hitachi Medical Corporation, Tokyo (JP)

( * ) Notice: Subject to any disclaimer, the term of this patent is extended or adjusted under 35 U.S.C. 154(b) by 353 days.

(21) Appl. No.: 10/344,430

(22) PCT Filed: Aug. 13, 2001

(86) PCT No.: PCT/JP01/07024

§ 371 (c)(1),
(2), (4) Date: Feb. 11, 2003

(87) PCT Pub. No.: WO02/13693

PCT Pub. Date: Feb. 21, 2002

(65) Prior Publication Data

US 2004/0010191 A1    Jan. 15, 2004

(30) Foreign Application Priority Data

Aug. 11, 2000 (JP) .............................. 2000-244249

(51) Int. Cl.
*G01R 33/20* (2006.01)
*G01V 3/00* (2006.01)
*A61B 5/055* (2006.01)

(52) U.S. Cl. ...................... 324/307; 324/309; 600/410

(58) Field of Classification Search ........ 324/307–312, 324/300, 318
See application file for complete search history.

(56) References Cited

U.S. PATENT DOCUMENTS

| | | | | |
|---|---|---|---|---|
| 4,661,775 | A | * | 4/1987 | Kormos et al. ............. 324/307 |
| 5,432,447 | A | * | 7/1995 | Song .......................... 324/309 |
| 5,485,085 | A | * | 1/1996 | Sumanaweera et al. ..... 324/307 |
| 5,701,074 | A | * | 12/1997 | Zhu ........................... 324/307 |
| 6,150,973 | A | * | 11/2000 | Pritt .......................... 342/25 C |
| 6,177,795 | B1 | * | 1/2001 | Zhu et al. .................... 324/307 |
| 6,263,228 | B1 | | 7/2001 | Zhang et al. |
| 2004/0010191 | A1 | * | 1/2004 | Yatsui ......................... 600/410 |

FOREIGN PATENT DOCUMENTS

JP       2000-70239       3/2000

OTHER PUBLICATIONS

International Search Report in connection with corresponding International Application No. PCT/JP01/07024.

(Continued)

*Primary Examiner*—Diego Gutierrez
*Assistant Examiner*—Tiffany A. Fetzner
(74) *Attorney, Agent, or Firm*—Cooper & Dunham LLP

(57) ABSTRACT

A magnetic resonance imaging method for fully automatically forming a water/fat separated image by calculation after acquiring data on images of different echo times, wherein the unwrapping of a phase map showing the distribution of the phase rotation due to the inhomogeneous static magnetic field is repeated so as to determine the distribution of the inhomogeneous static magnetic field by using an index used for judging whether or not the unwrapping is properly being performed, and wherein during the formation of a water/fat separated image with correction of the static magnetic field, the unwrapping is automatically and properly performed in correcting the static magnetic field, and the water/fat images are automatically discriminated.

19 Claims, 14 Drawing Sheets

OTHER PUBLICATIONS

W. Thomas Dixon (1984) "Simple Proton Spectroscopic Imaging[1]", Radiology, vol. 153, pp. 189-194.

M. Patel and X. Hu (1993) "Direct Calculation Of Wrap-Free Phase Image", Proceedings Of Annual Meetings of the Society of Magnetic Resonance in Medicine (=SMRM), No. 721.

Jerry Szumowski et al. (1994) "Phase Unwrapping in the Three-Point Dixon Method for Fat Suppression MR Imaging[1]", Radiology, vol. 192, pp. 555-561.

Qing-San Xiang and Li An (1995) "Water-Fat Imaging with Three-Point Direct Phase Encoding", Proceedings, SMR 3rd Meeting, p. 658.

Li An and Qing-San Xiang (1996) "Quadrature 2-Point Water-Fat Imaging", Proceedings, ISMRM 4th Scientific Meeting, p. 1541.

Bernard D. Coombs et al. (1997) "Two-Point Dixon Technique for Water-Fat Signal Decomposition with B0 Inhomogeneity Correction", Magnetic Resonance in Medicine, vol. 38, pp. 884-889.

Li An and Qing-San Xiang (1998) "Water-Fat Imaging with Three Orthogonal-Phase Acquisitions", Proceedings, ISMRM 6th Scientific Meeting, p. 1866.

* cited by examiner (a) BEFORE UNWRAP
(b) AFTER UNWRAP
(c) DIFFERENCE IMAGE

1ST ECHO THRESHOLD
VALUE MASK + LOOP MASK

COMPARISON ec2/ec1MASK + LOOP MASK

UNWRAP PROCESSED STATE

MAGNETIC RESONANCE METHOD WHICH AUTOMATICALLY FORMS WATER/FAT SEPARATED IMAGES WITH DIFFERENT ECHO TIMES AND DETERMINES THAT PROPER PHASE UNWRAPPING HAS BEEN UTILIZED

FIELD OF THE INVENTION

The present invention relates to a magnetic resonance imaging device (hereinafter will be referred to as MRI device) and method, and, more particularly, relates to an MRI device and method which achieves an automatic separation between water imaging and fat imaging.

BACKGROUND ART

An imaging object of an MRI device which becomes widespread in clinical application is protons which are a major constituent material of an inspection subject. Through imaging such as a spatial distribution of proton density and a spatial distribution of relaxation attenuation of excitation state, configurations or functions of such as a human head, abdomen and extremity are imaged in two dimension or three dimension.

Protons exist such as in water and fat in human tissue, however, their chemical shifts differ depending on their combination configurations. By making use of such chemical shift difference many approaches of drawing separately an image of protons in water and an image of protons in fat have been proposed. For example, as an example method of acquiring a fat suppressed image, a method, in which a plurality of images having different echo times (TE) are obtained and then water and fat separated images are acquired through computation thereof, is enumerated. A typical method therefor is disclosed in "Simple Proton Spectroscopic Imaging" by W. Thomas Dixon et al., (RADIOLOGY Vol. 153, pp 189–194 (1984)), which hereinbelow will be referred to as Dixon method. Methods of acquiring water and fat separated images through computation other than Dixon method are known and disclosed, for example, in the following papers "Water-Fat Imaging with Three-Point Direct Phase Encoding" by Qing-San Xiang and Li An, (Proc., SMR 3rd Meeting. p 658 (1995)), "Quadrature 2-point Water-Fat Imaging", by Li An and Qing-San Xiang, (Proc., ISMRM 4th Scientific Meeting, p 1541 (1996)), and "Water-Fat Imaging with Three-Orthogonal-Phase Acquisitions" by Li An and Qing-San Xiang, (Proc., ISMRM Scientific Meeting, p 1866 (1998)).

These methods are common in the following aspect, in which image data of a plurality of images are acquired from a plurality of echo signals having different times (echo time TE) from nuclear spin excitation to generation of signals and the imaging is performed by separating water signals and fat signals through computation of the acquired image data.

These methods in which the water and fat separated images are acquired by performing computation with regard to the plural images prepared from the plural signals having such different echo times TE include the following problems. One problem is that an unintended phase offset is caused in the signal due to such as inhomogeneous static magnetic field and local magnetic field turbulence, and another problem is that an image obtained by the computation is difficult to discriminate between a water image and a fat image.

The first problem is caused by such as distortion of a magnet which generates the static magnetic field and the performance limitation of the magnet itself as well as may be caused by magnetic susceptibility difference in respective portions of an inspection subject, when the same being placed in an MRI device. A static magnetic field inhomogeneity in Field of View (FOV) of an MRI image causes to vary frequencies of MR signals and causes an image quality deterioration such as a position displacement and flow in the acquired image. Further, because of phase variation in images due to the static magnetic field inhomogeneity it is difficult of obtain a correct result, when performing a complex computation between images.

In connection with the above referred to water and fat image separation, as a method of resolving the problem with regard to the phase offset due to the static magnetic field inhomogeneity, such as 2-point Dixon method and 3-point Dixon method in which a function of correcting the influence due to the static magnetic field inhomogeneity is added to the Dixon method are proposed, for example, in "Two-Point Dixon Technique for Water-Fat Signal Decomposition with B0 Inhomogeneity Correction" by Bernard D. Cooms et al., (Magnetic Resonance in Medicine, Vol. 38, pp 884–889 (1997)).

The above referred to method will be explained in connection with 2-point Dixon method. In the 2-point Dixon method, signals are acquired at timings when phases of proton in water and proton in fat are in in-phase and in anti-phase due to their chemical shift difference as illustrated in FIG. 1. In FIG. 1, 102 and 103 are respectively gradient magnetic field pulses for generating echo signals S1 and S2, and in the signal S1 a signal component 105 from water protons and a signal component 104 from fat protons are contained and in the signal S2 a signal component 107 from water protons and a signal component 106 from fat protons are contained.

Herein, the timing of acquiring the first echo signal (first echo) S1 is determined at a timing when $2n\tau$ (wherein n is a positive integer, which is also true throughout the present specification) has elapsed after a high frequency magnetic field pulse 101 is generated, wherein when assuming difference of resonance frequencies of water protons and fat protons is $\Delta f$, $2\tau = 1/\Delta f$, and the timing of acquiring the second echo signal (second echo) S2 is when $\tau$ has elapsed after the first echo.

When no phase offset due to the above referred to static magnetic field inhomogeneity is induced until the acquisition of the first and second echoes after generation of the high frequency magnetic field pulse 101, a water image and a fat image are obtained through computation between an image (first echo image) obtained from the first echo signal and an image (second echo image) obtained from the second echo signal according to the following equations:

$$S1(x,y) = W(x,y) + F(x,y) \quad (1)$$

$$S2(x,y) = W(x,y) - F(x,y) \quad (2)$$

$$S1(x,y) + S2(x,y) = 2W(x,y) \quad (3)$$

$$S1(x,y) - S2(x,y) = 2F(x,y) \quad (4)$$

wherein, S1(x, y) represents the first echo, S2(x, y) represents the second echo, and W(x, y) and F(x, y) respectively represent magnitudes of signal due to water protons and of signal due to fat protons in the respective echo signals.

Now, when a phase offset exists in the signals, the first echo signal and the second echo signal are expressed as follows;

$$S1(x,y)=(W(x,y)+F(x,y))\exp(i(\alpha(X,y))) \quad (5)$$

$$S2(x,y)=(W(x,y)-F(x,y))\exp(i(\alpha(X,y)+\phi(x,y))) \quad (6)$$

wherein, $\alpha(x, y)$ is a phase rotation component due to such as inhomogeneity of RF magnetic field pulse in the vector direction, but independent from time and, in the case of the gradient echo (GrE) sequence as illustrated in FIG. 1, contains a phase rotation component caused during the time TE (wherein $2n\pi$) due to the static magnetic field inhomogeneity, and $\phi(x, y)$ is a phase rotation component due to the static magnetic field inhomogeneity.

As will be seen from the above, where there exists a static magnetic field inhomogeneity, a difference in phases of the first echo and the second echo is caused, thereby, the water signal and the fat signal can not be separated through the simple addition and subtraction as with the equations (3) and (4). Accordingly, in the Dixon method in which the function of correcting the influence due to the static magnetic field inhomogeneity is added, at first a phase offset $\phi(x, y)$ due to the static magnetic field inhomogeneity is determined through computation between two echoes, then, after correcting the phase offset, the water and fat image separation is performed through addition and subtraction.

The 2-point Dixon method with static magnetic field correction makes use of the fact that the phase difference between a water signal and a fat signal in S2 signal is $\pi$ in order to determine the phase offset. Namely, when doubles $\pi$ makes $2\pi$, therefore, in view of principal value rotation the doubled value becomes equivalents to that with no rotation. Therefore, through subtracting the phase of $S1(x, y)$ from that of $S2(x, y)$ and doubling the resultant difference, a static magnetic field inhomogeneity map can be determined.

Further, in 3-point Dixon method three signals S1, S2 and S3 each having different echo time is obtained as shown in FIG. 2 and a phase rotation amount $2\phi(x, y)$ is determined depending on a ratio between the first echo S1 and the third echo S3 in which the water signals and the fat signals are in in-phase. In FIG. 2, 202, 203 and 204 are respectively gradient magnetic field pulses for causing the echo signals S1, S2 and S3, and 206, 209 and 212 are water signals and 205, 208 and 211 are fat signals.

When determining the phase rotation amount due to the static magnetic field inhomogeneity in such Dixon methods with static magnetic field correction, a processing for eliminating the principal value rotation, namely a processing called as unwrapping or rewinding is required. Methods of unwrap processing are disclosed in the above referred to papers as well as the following papers; "Direct Calculation of Wrap-Free Phase Image" by M. Patel and X. Hu, (Proceedings of Annual Meetings of the Society of Magnetic Resonance in Medicine (=SMRM). No. 721, (1993)) and "Phase unwrapping in the Three Point Dixon Method for Fat Suppression MR Imaging" by Jerzy Szmowski et al., (Radiology, Vol. 192, pp 555–561 (1994)).

However, such unwrapping (rewinding) shows a problem of being susceptible to influence of noises. In particular, with regard to the 2-point Dixon method since the second echo signal has to be obtained at the timing when the phases of the water protons and the fat protons are in anti-phase, the difference between the water signal and the fat signal forms the second echo signal, therefore, of which intensity is small which is significantly affected by noises. In order to eliminate such influence of noises, some measures such as omitting the unwrap processing by masking regions which are susceptible to noises is necessitated, however, since such regions which are susceptible to noises vary depending on respective images, it was difficult to set and select proper noise removal masks for every unwrap processing.

With regard to the second problem that it is difficult to discriminate whether an image obtained by the computation is a water image or a fat image, such discrimination is theoretically possible, if the unwrap starting point is optimized in order to eliminate the phase offset of $2n\pi$ caused in association with the unwrap processing. However, since there are no methods of optimizing automatically the unwrap starting point, measures of such as visually designating the starting point and of deciding which is the water image by visually observing the resultant image are taken and any automatic separation between a water image and a fat image is not realized until now.

Accordingly, an object of the present invention is to provide an MRI device provided with a function of acquiring a water image and a fat image through computation between images obtained from plural echo signals having different echo times which permits static magnetic field correction including a proper unwrap processing and further permits an automatic discrimination between the water image and the fat image. Thereby, another object of the present invention is to provide an MRI device which permits an automatic acquisition of separated water and fat images.

Further, still another object of the present invention is to provide an MRI method with imaging method including a static magnetic field correction processing in an MRI device which permits automatic optimization of unwrap processing.

DISCLOSURE OF THE INVENTION

In order to resolve the above tasks, an MRI device according to a first aspect of the present invention which is provided with a magnetic field generation means which respectively generates a high frequency magnetic field and a gradient magnetic field in a space where a static magnetic field is formed, a signal processing means which detects a nuclear magnetic resonance signal generated from an inspection subject placed in the space and reconstructs an image therefrom and a display means which displays the reconstructed image, characterized in that the signal processing means performs, by making use of at least more than one nuclear magnetic resonance signals having different times (TE) from irradiation of the high frequency signal and generation of the nuclear magnetic resonance signals, a computation for determining a phase offset distribution-between the signals, an unwrap processing for correcting a principal value rotation caused in the computation and at the same time performs a judgement whether the unwrap processing is proper by making use of a parameter representing the unwrap processing state.

In the unwrap processing according to the present invention, plural noise removal masks are employed and are applied in a step by step manner. Further, in parallel with advancement of the unwrap processing, a parameter indicating whether or not any inconsistency in the unwrap processing occurs is at the same time prepared, and the properness of the unwrap processing is judged based on the parameter. When it is judged that the unwrap processing is improper, another unwrap processing is performed by adding another type of noise removal-mask or by varying parameter (such as a threshold value used when preparing a mask) of the mask. When it is judged that the unwrap processing is proper based on the parameter indicating the unwrap processing state, the unwrap processing result is determined as the phase offset distribution. The phase offset distribution determined herein is typically caused by such as a static magnetic field inhomogeneity but sometimes includes those caused by such as a local phase turbulence.

The noise removal masks used in the unwrap processing according to the present invention include either one which is prepared from an absolute value image of the first echo signal, one which is prepared from an absolute value image of the second echo signal or one which is prepared from both the above, or a combination thereof.

Further, as a noise removal mask used in the unwrap processing according to the present invention, a mask (which will be hereinafter referred to as a loop mask) can be used which is obtained when scanning the entire images in such a manner that while assuming a closed loop on a map representing the phase rotation amount distribution due to the static magnetic field inhomogeneity, and when a phase difference accumulation value taken around the closed loop is $2n\pi$ (wherein n is a positive integer), the points on the closed loop are masked. Such loop mask can also be used in parallel with the above referred to masks prepared by the absolute value image of the first echo and/or the absolute value image of the second echo.

The above first aspect of the present invention can be applied to an MRI device provided with a function which, by making use of at least more than one nuclear magnetic resonance signals having different times (TE) from irradiation of the high frequency magnetic field to generation of the nuclear magnetic resonance signals, reconstructs an image with regard to two types of unclear spins having different chemical shifts through computation between the signals.

Namely, such MRI device is characterized, in that by making use of at least more than one types of nuclear magnetic resonance signals having different times (TE) from irradiation of the high frequency magnetic field to generation of the nuclear magnetic resonance signals, the signal processing means performs the computation for determining the phase offset distribution between the signals, the unwrap processing for correcting the principal value rotation caused in the computation and at the same time performs the processing of judging properness of the unwrap processing by making use of the parameter representing the unwrap processed state, further corrects the nuclear magnetic resonance signals based on the phase offset distribution of properly unwrap processed, thereafter, the image with regard to the two types of nuclear spins having different chemical shifts is reconstructed through the computation between the signals.

Further, an MRI device according to a second aspect of the present invention which is provided with a magnetic field generation means which respectively generates a high frequency magnetic field and a gradient magnetic field in a space where a static magnetic field is formed, a signal processing means which detects a nuclear magnetic resonance signal generated from an inspection subject placed in the space and reconstructs an image therefrom and a display means which displays the reconstructed image, characterized in that the signal processing means, by making use of at least more than one nuclear magnetic resonance signals having different times (TE) from irradiation of the high frequency signal and generation of the nuclear magnetic resonance signals, reconstructs more than one original images, further reconstructs two types of display images with regard to two types of nuclear spins having different chemical shifts through computation between these original images and performs an automatic discrimination on the correspondence between the obtained two types of the display images and the two types of the nuclear spins from a ratio of pixel values of the more than one original images and/or pixel values of the two types of the display images.

When reconstructing the two types of images (display images) through the computation (addition and subtraction) between the images (original images) obtained from the signals having different echo times, by making use of two parameters, namely (1) a ratio of pixel values of more than one original images, and (2) pixel values of the two types of the display images, the types of the display images can be correctly discriminated. More specifically, these two parameters are determined (1) through comparison of the ratios of signal values of two original images in an intense signal region which are respectively extracted from an addition image obtained by adding the original images and a subtraction image obtained by subtracting the original images and (2) through comparison of the pixel values in an intense signal region which are respectively extracted from the addition image and the subtraction image.

The two types of display images are typically the water image and the fat image, however, the same can be likely applied to materials such as water and silicon and water and NAA to which the chemical shift difference can be made use of.

Further, an MRI device according to a further aspect of the present invention which is provided with a magnetic field generation means which respectively generates a high frequency magnetic field and a gradient magnetic field in a space where a static magnetic field is formed, a signal processing means which detects a nuclear magnetic resonance signal generated from an inspection subject placed in the space and reconstructs an image therefrom and a display means which displays the reconstructed image, characterized in that the signal processing means performs, by making use of at least more than one nuclear magnetic resonance signals having different times (TE) from irradiation of the high frequency signal and generation of the nuclear magnetic resonance signals, a computation for determining a phase offset distribution between the signals, an unwrap processing for correcting a principal value rotation caused in the computation and at the same time performs a judgement whether the unwrap processing is proper by making use of a parameter representing the unwrap processing state, and further, by making use of the nuclear magnetic resonance signals corrected based on the phase offset distribution judged as properly unwrap processed, reconstructs more than one original images, further reconstructs two types of display images with regard to two types of nuclear spins having different chemical shifts through computation between these original images and performs an automatic discrimination on the correspondence between the obtained two types of the display images and the two types of the nuclear spins from a ratio of pixel values of the more than one original images and/or pixel values of the two types of the display images.

The above MRI device can realized an automatic operation by means of the incorporation of an automatic optimization processing of the unwrap processing and an automatic discrimination processing of the display images, when reconstructing the two types of images (display images) through the computation between the images (original images) obtained from the signals having different echo times.

The MRI device according to the present invention can be simply applied to the 2-point Dixon method with static magnetic field correction, thereby, separated water and fat images can be obtained in a full automatic manner. Further, since the measurement time of 2-point Dixon method is short in comparison with that by 3-point Dixon method, thereby, the repetition time (TR) of the sequence can be shortened. Thus, when assuming that the repetition times (TR) are the same, the number of images obtained in multi-slices can be increased. Still further, since direct correction of the phases between two data is performed, influences such as due to eddy current can be eliminated in 100%, thereby, the present invention is suitable for an open type MRI device in which such as static magnetic field inhomogeneity and magnetic field turbulence due to gradient magnetic field coils are significant.

BEST EMBODIMENTS FOR CARRYING OUT THE PRESENT INVENTION

Hereinbelow, embodiments of the present invention will be explained with reference to the drawings. Further, among the drawings which will be used for the explanation below, FIGS. 8, 11, 13, 14, 19 and 20 are photos which are prepared in image forms for explaining processings performed in the present embodiments.

Figure 3:
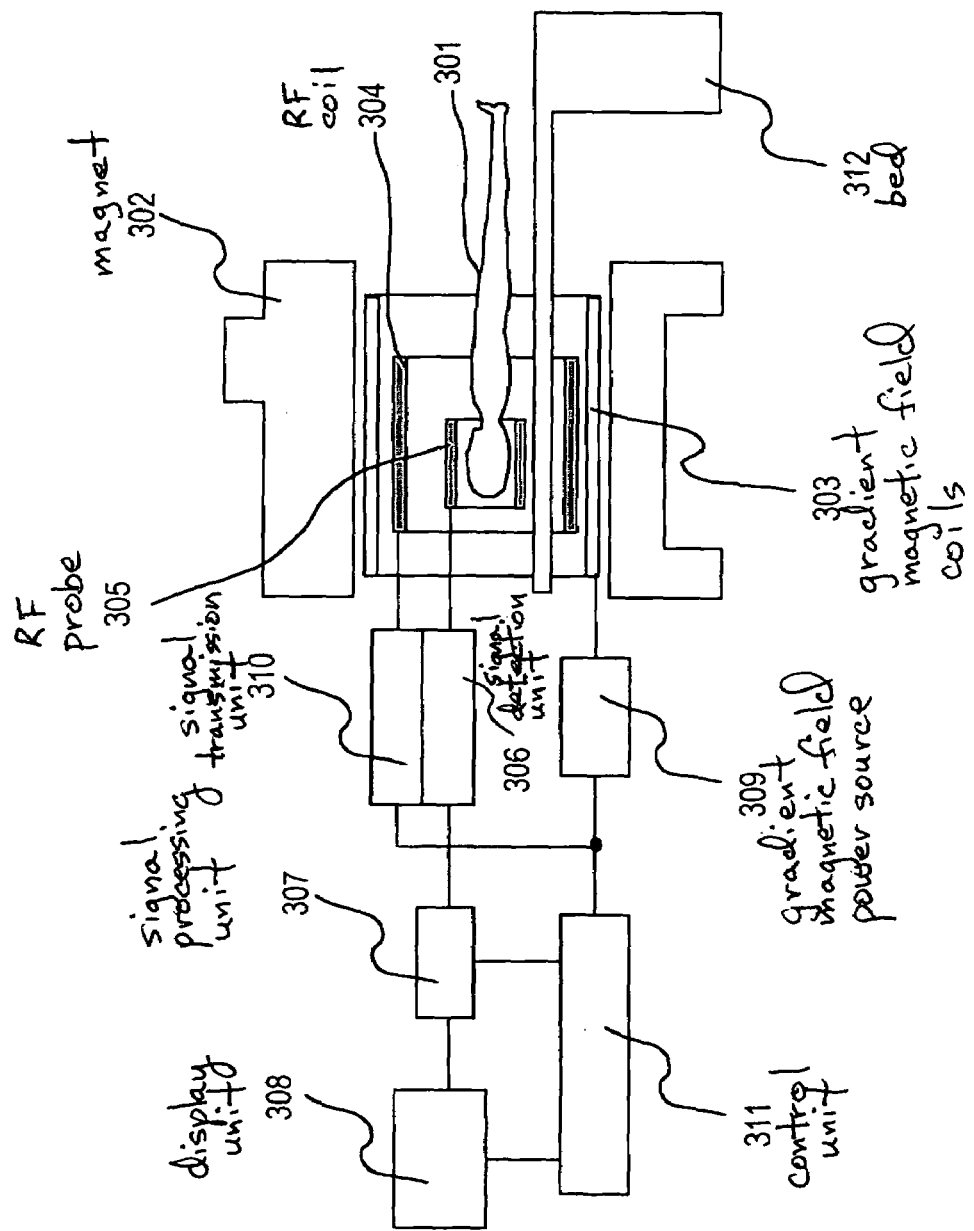
FIG. 3 is a schematic diagram of an MRI device to which the present invention is applied.

FIG. 3 shows a constitutional diagram of an MRI device to which the present invention is applied. The MRI device is provided with a magnet 302 which generates a static magnetic field in a space surrounding an inspection subject 301, a gradient magnetic field coils 303 which induce magnetic field gradients in the space in three directions of X, Y and Z, an RF coil 304 which generates a high frequency magnetic field for causing nuclear spins of atoms constituting the tissue of the inspection subject 301 a nuclear magnetic resonance and an RF probe 305 which detects NMR signals generated from the inspection subject 301 by the nuclear magnetic resonance. The MRI device is further provided with a gradient magnetic field power source 309 serving as a power source for the gradient magnetic field coils 303, a signal transmission unit 310 which drives the RF coil 304, a signal detection unit 306 which detects the NMR signals from the RF probe 305, a signal processing unit 307 which processes the signals, a control unit 311 which controls the gradient magnetic field power source 309, the signal detection unit 306 and the signal processing unit 307, and a display unit 308 which displays the processed result by the signal processing unit 307. A bed 312 is for laying the inspection subject 301 thereon.

In such constitution, after carrying in the inspection subject 301 into a space of homogeneous static magnetic field produced by the magnet 302, the RF coil 304 generates in response to the signals from the RF signal transmission unit 310 high frequency magnetic fields having frequencies which cause nuclear spins of atoms (hereinbelow will be referred to simply as spin) constituting the tissue of the inspection subject 301 nuclear magnetic resonances. The objective spins in the present embodiment are protons which are the major constituent material of the inspection subject 301.

The gradient magnetic field coils 303 are constituted by gradient magnetic field coils in three directions of X, Y and Z and generate respective magnetic fields in response to signals from the gradient magnetic field power source 309. With the gradient magnetic field a region of the inspection subject 301 where the nuclear magnetic resonances are caused is selected as well as positional information is provided for the NMR signals.

The signals from the RF probe 305 are detected by the signal processing unit 307 and further converted into image signals through computation. The images are displayed on the display unit 308.

The control time chart, which controls the generation of the above referred to high frequency magnetic field and the gradient magnetic fields and the measurement of the NMR signals, is called as pulse sequence, and which is stored in the control unit 311 as a preset program. In the embodiment of the present invention which will be explained hereinbelow, a pulse sequence so called 2-point Dixon method is executed in which at least two NMR signals having different echo times are measured in one sequence to be repeated, and an image which primarily draws water protons (hereinbelow will be referred to as water image) and an image which primarily draws fat protons (hereinbelow will be referred to as fat image) are obtained. Further, when reconstructing the images by having the NMR signals, a computation is added which corrects the static magnetic field inhomogeneity by making use of the two NMR signals having different echo times.

Hereinbelow, the signal measurement and the magnetic field correction computation according to the present embodiment will be explained in detail.

Figure 4:
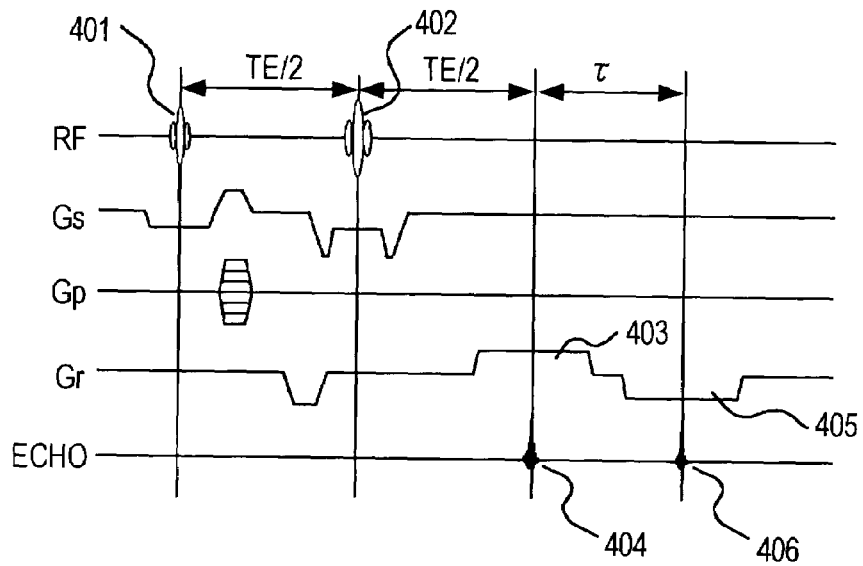
FIG. 4 is a time chart of data acquisition in a 2-point Dixon method which is employed in the present invention.

FIG. 4 shows a pulse sequence according to a 2-point Dixon method employed in the present embodiment. In this pulse sequence, at first an RF pulse 401 is irradiated to excite spins of an inspection subject. In this instance, a slice selection gradient magnetic field Gs for selecting a specific slice of the inspection subject is applied at the same time with the RF pulse 401. Subsequently, a phase encode gradient magnetic field Gp for phase-encoding the NMR signals is applied, and then another RF pulse 402 for inverting the spins is irradiated together with a slice selection gradient magnetic field Gs. Thereafter, a read-out gradient magnetic field Gr 403 is applied and after time TE from irradiation of the first RF pulse 401 an echo signal (first echo) is measured, and further another read-out gradient magnetic field Gr 405 of which polarity is inverted from the former is applied and after time T from the measurement of the first echo 404 an echo signal (second echo) 406 is measured.

The above sequence is repeated predetermined times, for example such as 128 times and 256 times, while varying the intensity of the phase encode gradient magnetic field Gp to obtain a necessary number of echo signals for an image reconstruction. Namely, with the sequences one image (first echo image) is formed by the first echoes of which number corresponds to the repetition number and another image (second echo image) is formed by the second echoes of which number also corresponds to the repetition number. These formed images are used as original images in a computation for determining a water image and a fat image which will be explained later.

Figure 1:
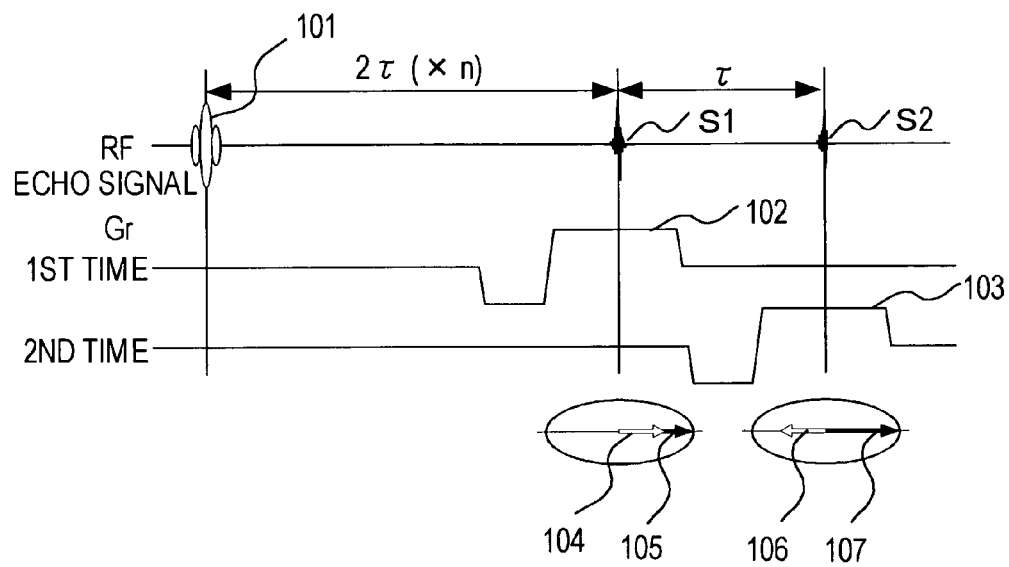
FIG. 1 is a time chart of data acquisition in a 2-point Dixon method.

Further, in FIG. 4 a spin echo type pulse sequence in which after irradiation of the RF pulse 401 the inverting RF pulse is used is exemplified, however, the gradient echo type pulse sequence as shown in FIG. 1 can also be used. Both in the spin echo type and gradient echo type pulse sequences, two signals having different echo times within one repetition time as shown in FIG. 4 can be measured as well as two signals having different echo times can be measured with twice measurements as shown in FIG. 1.

In such pulse sequence, at the timing when the first echo 404 is measured, the phases of the water proton spins (hereinafter will be referred to as water spin) and of the fat proton spins (hereinafter will be referred to as fat spin) are in in-phase, however, after lapsing time τ a phase offset is caused due to difference in resonance frequencies of the water spin and the fat spin, and after time τ the phases deviate by 180° each other.

Namely, since the water proton and fat proton perform precession with different frequencies fow and fof, the relative orientation of their magnetization vectors (spins) of the water protons and the fat protons is caused to offset in accordance with lapse of time. When assuming that the difference between the resonance frequencies of water protons and the fat protons is Δf, then 2τ=1/Δf, and when the water spins and the fat spins orient in the same direction at a certain moment, the same orient in the reverse direction (180°), in the same direction (360°) . . . after every τ.

In FIG. 4 pulse sequence, since the RF pulse 402 for inverting the spins is used, after time TE/2 from the irradiation of the RF pulse 402, the phases of the water spins and the fat spins are aligned and after elapsing τ the phases thereof are inverted each other.

As has been explained in Background Art, when assuming that image signals which are obtained by processing respectively these two NMR signals as S1(x, y) and S2(x, y) and the signal magnitudes due to water and fat among these signals are respectively as W(x, y) and F(x, y), the following equations (equations (1) and (2)) stand;

$$S1(x,y)=W(x,y)+F(x,y) \quad (1)$$

$$S2(x,y)=W(x,y)-F(x,y) \quad (2)$$

Accordingly, when adding S1(x, y) and S2(x, y), a water image as the addition image is obtained (equation (3)) and when subtracting the same, a fat image as the subtraction image is obtained (equation (4));

$$S1(x,y)+S2(x,y)=2W(x,y) \quad (3)$$

$$S1(x,y)-S2(x,y)=2F(x,y) \quad (4)$$

The precondition when the above equations (3) and (4) stands is that at the measurement timings of the first echo 404 and of the second echo 406, the phase relationship of the water spin and the fat spin is inverted and the phase of the water signal is unchanged, however, in reality due to such as static magnetic field inhomogeneity, the spin rotation is affected, which is expressed by the following equations;

$$S1(x,y)=(W(x,y)+F(x,y))\exp(i(\alpha(x,y))) \quad (5)$$

$$S2(x,y)=(W(x,y)-F(x,y))\exp(i(\alpha(X,y)+\phi(X,y))) \quad (6)$$

wherein, φ(x, y) is a phase rotation component due to the static magnetic field inhomogeneity and α(x, y) is a phase rotation component due to inhomogeneity of RF pulses in the vector direction.

Figure 5:
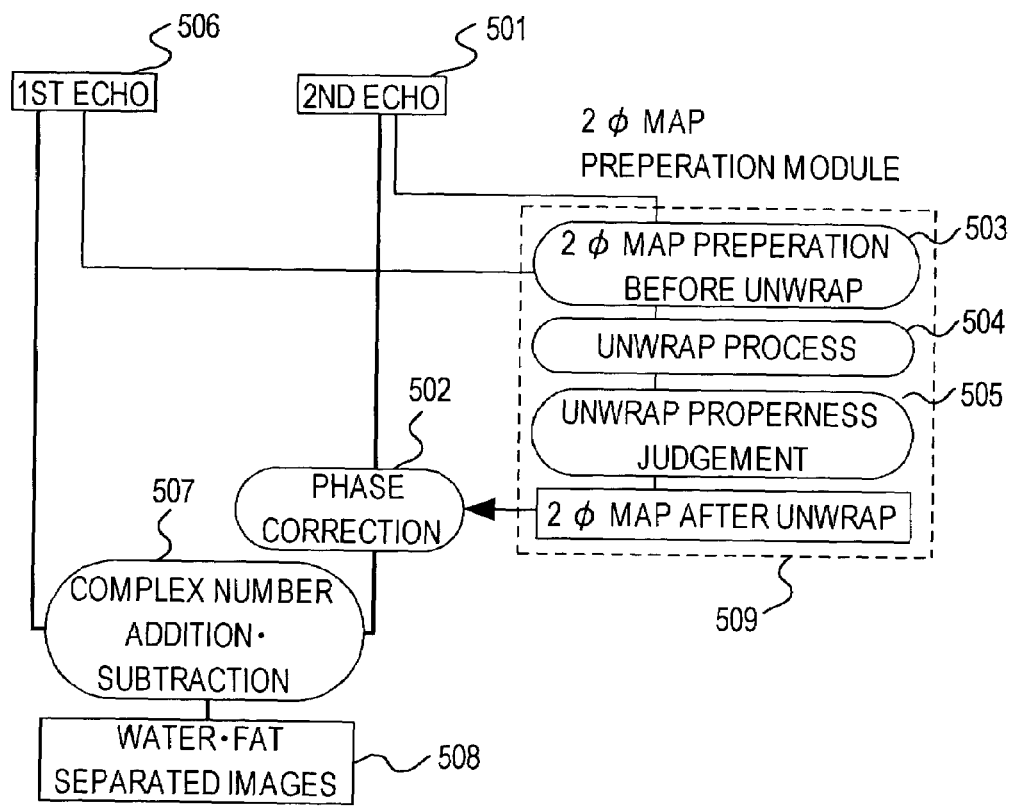
FIG. 5 is a diagram showing an example of a processing flow in a Dixon method with static magnetic field correction according to the present invention.

Accordingly, when obtaining the water image and the fat image by addition and subtraction of the first and second echoes 404 and 406, it is necessary to correct the phase rotation of the signals. For this purpose, the phase rotation amount φ is determined by making use of these two signals and with the determined phase rotation amount φ the processing for the phase correction is performed of which data processing algorism is shown in FIG. 5.

In this data processing, other than step 507 in which separated water and fat images are obtained through addition and subtraction of a first echo 506 and a second echo 501, a module 509, a portion surrounded by a dotted line, in which a phase 2φ map representing distribution of static magnetic field inhomogeneity is prepared by making use of these echoes 506 and 501 and step 502 which corrects the phase of the second echo 501 are included. The phase 2φ map is one which determines the phase rotation caused due to the static magnetic field inhomogeneity as a function of positions. After correcting the phase of the second echo based on the thus prepared phase 2φ map, the water and fat images 508 are obtained through the addition and subtraction processing 507.

The phase 2φ map preparation step 509 includes a phase 2φ map preparation before unwrap step 503, an unwrap processing step 504 and an unwrap properness judgement step 505. Hereinbelow, the function of the phase 2φ map preparation module will be explained in further detail.

At first, in the phase 2φ map preparation step 503 the phase of S1(x, y) is subtracted from that of S2(x, y) and the remained phase is doubled to determine a static magnetic field inhomogeneity map, which is expressed by the following equations;

$$S1^*(x,y)/|S1(x,y)|=\exp\{-i\alpha(X,y)\} \qquad (7)$$

$$S2(x,y)\times\{S1^*(x,y)/|S1(x,y)|\}=(W(x,y)-F(x,y))\exp\{i\phi(X,y)\} \qquad (8)$$

$$\{S2(x,y)\times(S1^*(x,y)/|S1(x,y)|)\}^2/S2(x,y)=\{(W(x,y)-F(x,y))^2/|W(x,y)-F(x,y)|\exp\{i2\phi(X,y)\}=|W(x,y)-F(x,y)|\exp(i2\phi(x,y)) \qquad (9)$$

when taken an argument of equation (9), 2φ(x, y) can be determined. Further, arg ( ) implies to determine the phase.

Subsequently, an unwrap processing is performed on the thus determined phase 2φ map. As will be well known, since phases "φ1" and "φ1+2π" are recognized as the same phase, when the phase distribution region exceeds over 2π, the phases "φ1" and "φ1+2π" can not be discriminated, thereby, discontinuous portions with regard to phase variation are caused (which is called as principal value rotation). The phase unwrap processing is a processing for eliminate such principal value rotation, more specifically, is a processing in which phases of a predetermined reference point and of an adjacent point (a point to be unwrapped) are respectively determined, and if the difference Δφ thereof is outside a predetermined range (usually −π≦Δφ≦π), it is determined that the principal value rotation has occurred, and 2π is added or subtracted to and from the phase value of the adjacent point. Alternatively, such processing is performed, in that after determining the phase difference between the reference point and the point to be unwrapped through complex computation and expressing the same as a phase value, the phase of the present point to be unwrapped is determined by adding the phase value to the phase of the reference point. In this instance, the point to be unwrapped can be directly determined without adding ±2π to the point to be unwrapped. These phase unwrap processings are usually performed for all of the pixels while successively changing the reference point.

In the present invention, such unwrap processing is not performed with regard to all of the coordinate points on the obtained phase map, but regions in which influences of noises are intense are excluded beforehand by making use of a proper noise removal mask and the unwrap processing is performed only over the remaining regions. This is because the phase rotation amount due to the static magnetic field inhomogeneity is determined by making use of the second echo which is obtained at the timing when phases of the water spin and the fat spin are in anti-phase, therefore, the amount of noise increases and artifact is likely to occurs, consideration of which is particularly important when the 2-point Dixon method is employed in the present invention.

In the present embodiment, as the noise removal mask the following masks are used in combination, (a) a mask (first echo threshold mask) which is prepared in such a manner that an absolute value of the first echo is determined and when the absolute value is more than a preset threshold value, the mask shows 1 and when less than the preset threshold value, the mask, shows 0, (b) a mask (second echo threshold mask) which is prepared in such a manner that an absolute value of the second echo is determined and when the absolute value is more than a preset threshold value, the mask shows 1 and when less than the preset threshold value, the mask shows 0, and (c) a loop mask which is prepared in such a manner that a closed loop is assumed on the phase distribution map and when the accumulated phase difference value around the closed loop is 2nπ, the points on the closed loop are determined 0 (in other words pop-up points are patched).

In the unwrap properness judgement step 505, properness of unwrapping result after effecting the above referred to masking is judged, and if it is judged the unwrap processing is not properly performed, another unwrap processing is again performed which changes the condition of masking, and the same processing (504 and 505) is repeated until a proper unwrap processing is effected.

Figure 6:
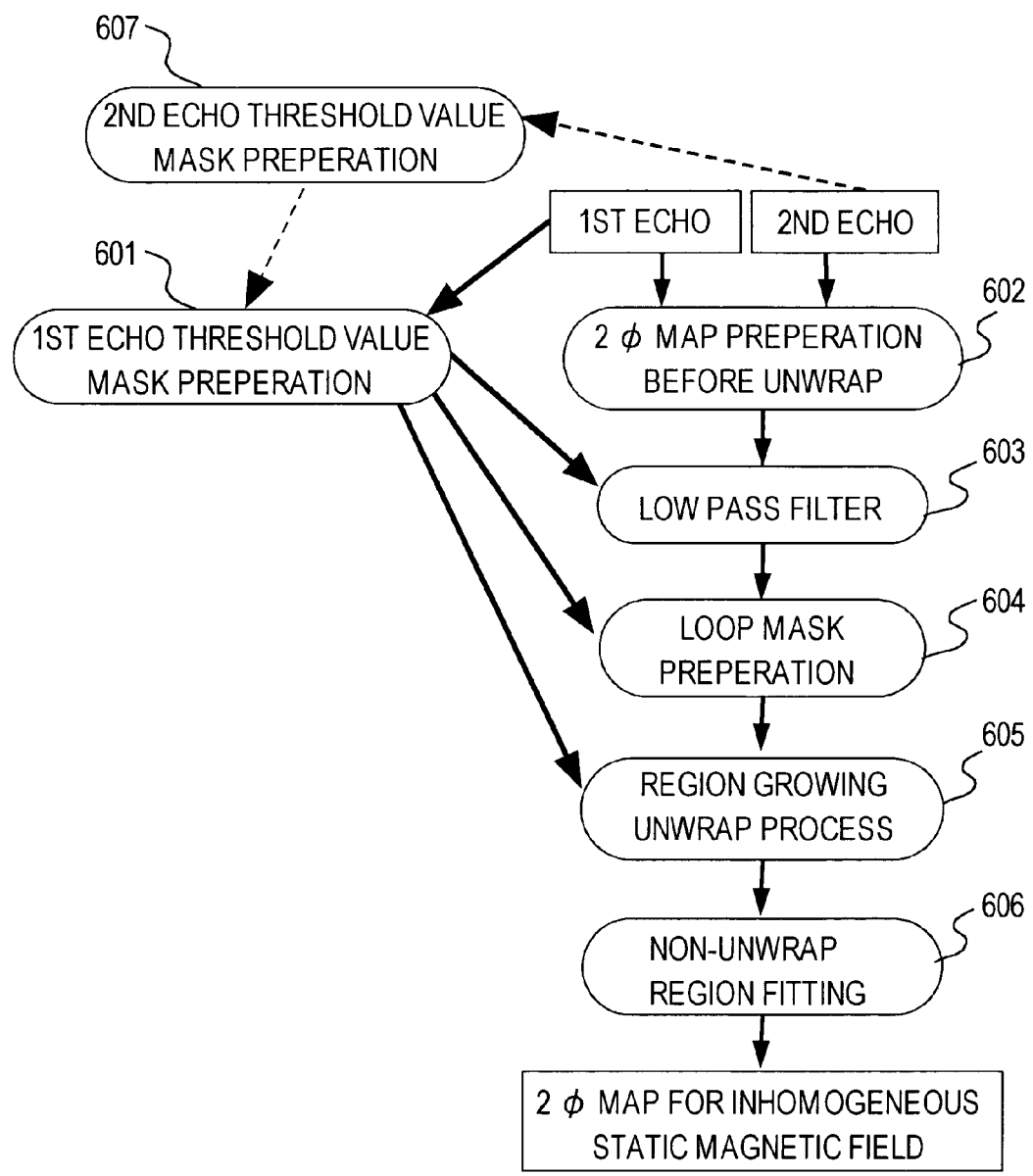
FIG. 6 is a diagram showing an example of phase 2φ map preparation flow according to the present invention.

FIG. 6 is a diagram showing a processing flow in the phase 2φ map preparation module, and in the illustrated embodiment, at first prior to the unwrap processing the first echo threshold mask is prepared from the first echo (step 601), the prepared mask is applied to the phase 2φ map prepared at step 602 and only a portion where the inspection subject exists is extracted among the phase 2φ map. Subsequently, in order to advance the unwrap processing smoothly, the phase 2φ map prior to the unwrapping is smoothed by making use of a low pass filter (LPF) 603.

The subsequent unwrap processing module includes a loop mask preparation module 604 serving as the noise removal mask for the phase 2φ map, a region growing unwrap processing algorism 605 and a fitting module 606 for non-unwrap region.

Figure 7A:
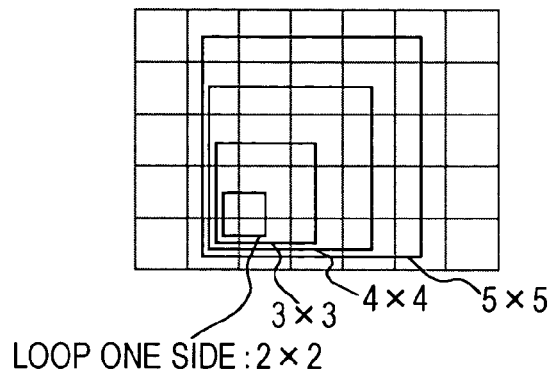
FIGS. 7(a) and (b) are diagrams for explaining a loop mask according to the present invention.
Figure 7B:
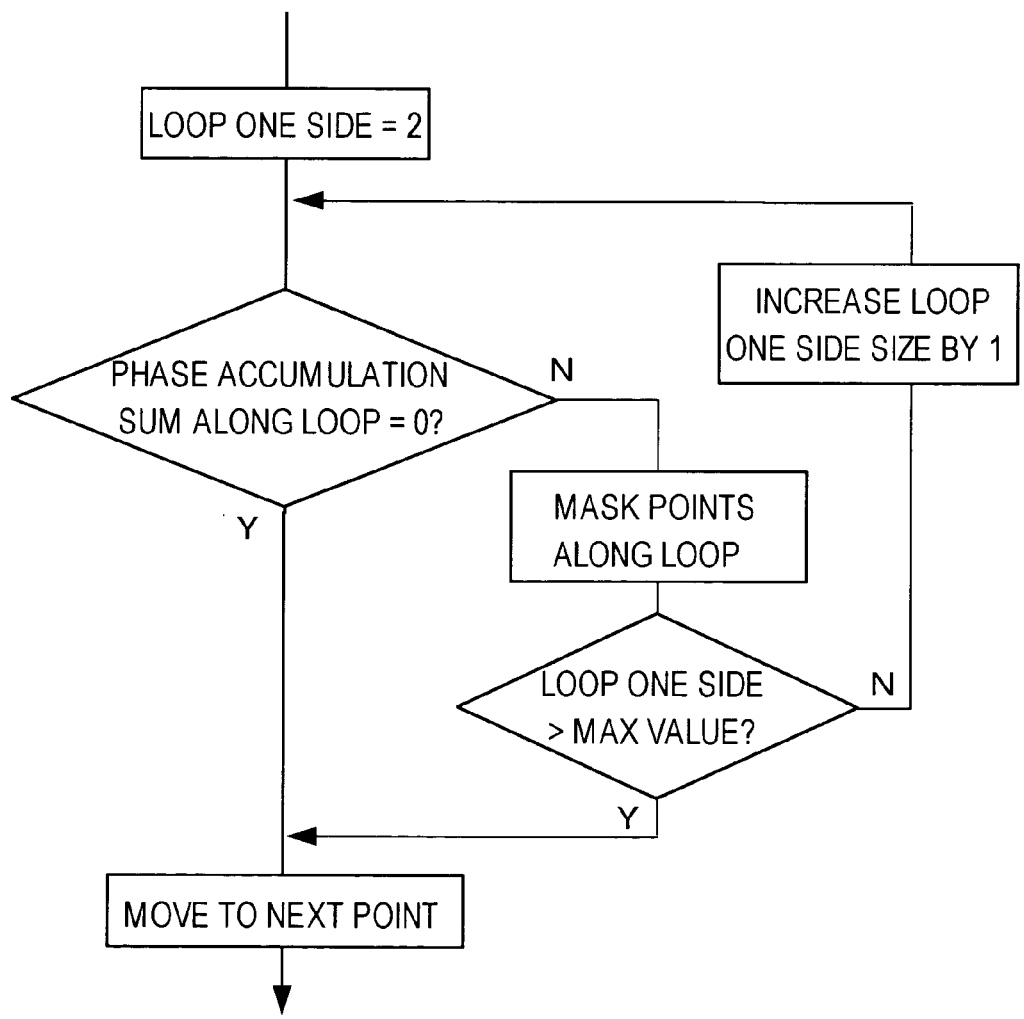

As shown in FIGS. 7(a) and 7(b), the loop mask preparation module 604 prepares a loop having sides of a predetermined length, for example, a loop of 2×2, while using a certain point (in the drawing a pixel indicated in gray color) as a reference and phase sum (an accumulation sum of the phase differences with adjacent pixels) of the points on the loop. If no phase disturbance due to noises exists, the phase sum is naturally 0, therefore, if the determined phase sum is 0, the reference point is shifted without masking and the same processing is repeated. On the other hand, if the phase sum is not 0, it is understood that a disturbance in phase is caused, therefore, points on the loop are masked. Then, length of one side of the loop is increased, for example, 3×3 loop is formed and the phase sum of the points on the new loop is determined, if the phase sum is not 0, the length of one side is further increased. In this manner, the processing is repeated while expanding the loop until the phase sum of the points on the loop becomes 0. Further, when the length of one side of the loop reaches a predetermined maximum value, such processing is terminated and the reference point is shifted.

Generally, when the maximum value of one side of a loop mask is too small, regions which affect noises can not be properly removed, on the other hand, when the maximum value is too large, the unwrap processing can not be performed properly. Accordingly, in the present embodiment the maximum value of one side is set as small as possible at the first time and when it is judged at the unwrap properness judgement step 505 that the unwrap processing is not performed properly, the maximum value is gradually increased. With this measure, a masking beyond the necessity is prevented.

As has been explained previously, the region growing unwrap processing algorism 605 is a processing in which while selecting a predetermined point as a starting point, the phase differences between adjacent points including the starting point is successively investigated and when the phase difference is outside the predetermined range, 2π is added or subtracted to the phase of the concerned adjacent point or alternatively, after determining the phase difference between the reference point and the point to be unwrapped through complex computation and expressing the same as a phase value, the phase of the concerned adjacent point is determined by adding the phase value to the phase of the reference point. Candidates of the starting point which serves as the first reference point are picked out from points near center portion of FOV and one of the candidates on which the unwrap processing is most frequently performed is determined as the starting point. Thereby, an accuracy of the unwrap processing can be increased.

In the fitting module 606 of the non unwrap region, a processing, in which a phase value with regard to regions not effected unwrap processing is determined through function fitting, is performed. The function fitting is performed in two dimension.

Figure 8:
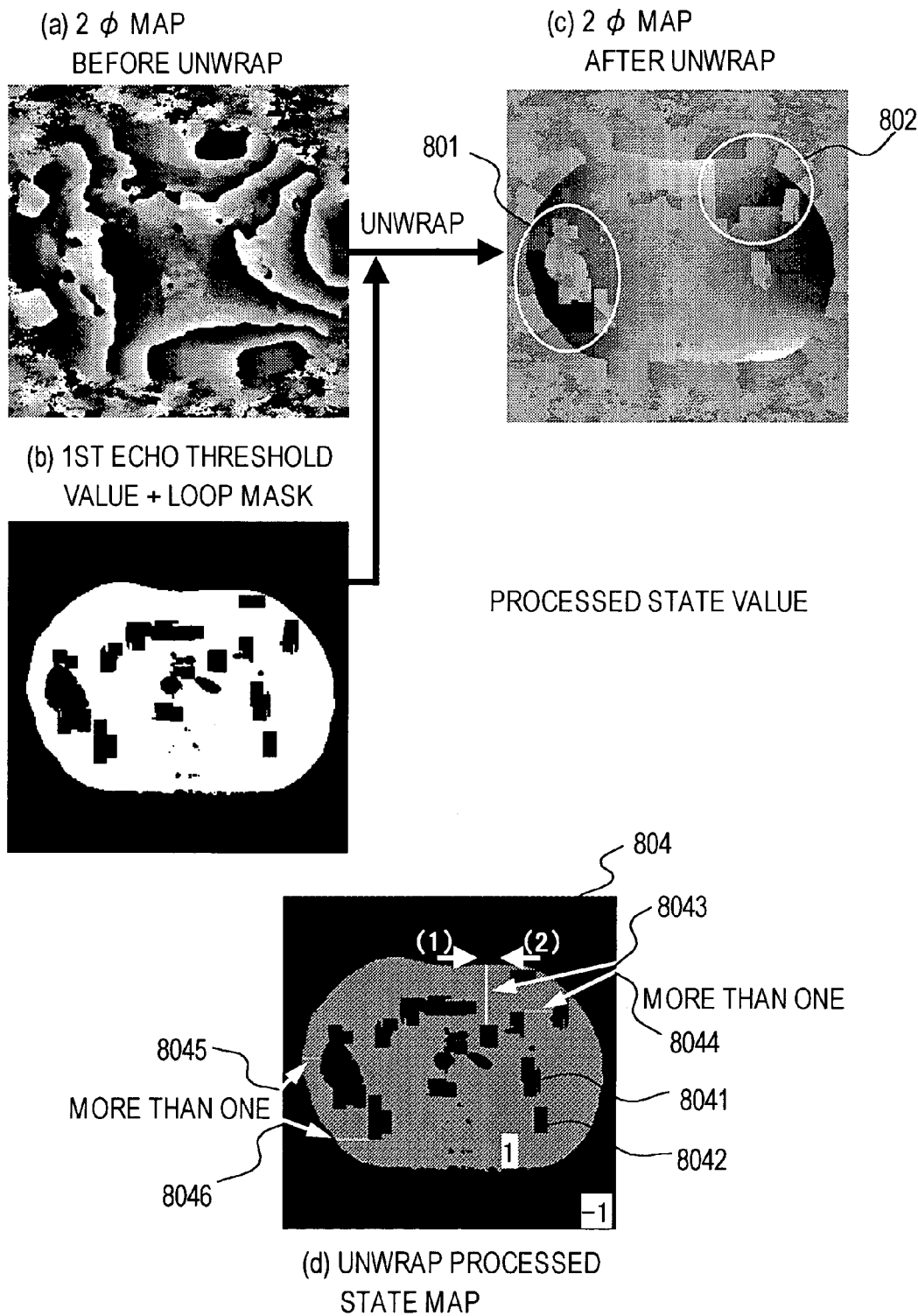
FIGS. 8(a) through (d) are diagrams showing in image forms an unwrap processing state according to the present invention.

FIG. 8 shows in image forms a phase map which is the object for the unwrap processing and a mask prepared prior to the unwrap processing. FIG. 8(a) shows a phase map before unwrap processing, and FIG. 8(b) shows a composition of the first echo threshold value mask and the loop mask. Black rectangular regions within the inspection subject region indicated in white represent regions masked by the loop masks. FIG. 8(c) shows a result of unwrap processing by making use of these masks. In the example as illustrated, on regions 801 and 802 surrounded by white lines discontinuous portions with regard to phase variation are caused because of improper unwrap processing. As in the above example, when the result of the unwrap processing under a predetermined condition is improper, the processing according to the fitting module is prevented and a further unwrap processing is performed after changing the mask condition. The changing of the mask condition includes alternation of the aforesaid loop mask and addition of the second echo threshold value mask, in that (a) ON/OFF of the second echo threshold value mask processing and (b) changing of "maximum value of one side" used in the loop mask 604 are included. According to the study of the present inventors, the above (a) and (b) affect significantly on the unwrap processing result, and the necessity of automatic unwrap processing including mask changing and unwrap processing properness judgement is confirmed.

The second echo threshold value mask 607 was introduced according to the following knowledge. Namely, since the second echo signal is expressed according to equation (2), in a region (W(x, y)~F(x, y)) in which the intensities of water signal W(x, y) and the fat signal F(x, y) are substantially the same which exist between a region (W>F) where the water signal intensity W(x, y) is larger than the fat signal intensity F(x, y) and a region (W<F) where the fat signal intensity is larger than the water signal intensity, the signal intensity S2(x, y) comes close to 0 and the signal is buried under noises. Thereby, the phase of the second echo signal is disturbed by the noises which causes unwrap error of the 2φ map. Therefore, a mask image is prepared with regard to the second echo absolute value image in which a portion exceeding a constant threshold value is determined as 1 and a portion below the constant threshold value is determined 0. With this mask the portion W(x, y)~F(x, y) can be removed.

Now, the unwrap processing properness judgement step (step 505 in FIG. 5) which judges whether or not the unwrap processing 605 with the region growing method which makes use of the above mask will be explained. In this step in parallel with the unwrap processing the unwrap processing state map 804 as shown in FIG. 8(d) is prepared and then based on the unwrap processing state map 804 it is judged whether the unwrapping is performed properly and if it is judged that the unwrapping has been performed improperly, the masking condition is altered.

A preparation method of the unwrap processing state map 804 will be explained with reference to FIG. 9.

At first, when performing the unwrap, a map (processing state map) (b) having the same number of pixels as the objective phase 2φ map (a) is prepared, and the processing information performed is written therein. In this map the following processing state values are written as the initial values;

unwrap processing object pixel (not masked pixel): 0
unwrap non-processing object pixel (masked pixel): 1

All of the illustrated pixels in the drawing are not masked and are unwrap processing object pixels. Herein, as shown in (a) in FIG. 9, selecting (1) as the unwrap starting point, the unwrap processing is performed with respect to adjacent four points in up and down and right and left directions ((2), x, (3) and (4)). When starting the unwrapping, it is assumed that the unwrap processing has been completed only at the starting point (1) and only the corresponding pixel is given the processing state value of 1. At this moment since the adjacent four points representing comparison points are not yet subjected to the unwrap processing, their processing state value is 0 (a processing state map representing the instant state is not illustrated). At the timing when the unwrap processing with respect to the adjacent points has been completed as shown in (a) of FIG. 9, the values indicating the processing state as shown in (b) of FIG. 9 is given. The processing state value is determined in the following manner depending on the unwrap processing of the points to be compared.

(i) when the processing state value of a comparison point is 0;

Phase difference from the reference point <0.5π, . . . perform unwrapping: processing state value=1 (condition 1)

Phase difference from the reference point >0.5π, . . . prevent unwrapping: processing state value=−2 (condition 2)

The condition 2 implies to skip the unwrap processing, because when the phase difference from the reference point is large, possibility of causing unwrap error is high. In this instance, the numbers of (2), (3) and (4) are assigned according to the order of unwrapping and mark X indicates that the unwrap processing was not performed. The point indicated by mark X is not used as a reference point in the successive region growing operation.

Subsequently, the same processing is performed while shifting a reference point to (2) as shown in (c) of FIG. 9. Namely, processing state values are given to the adjacent points (5), (6) and (7) with respect to the position of (2) according to the above conditions 1 and 2. Although the position (1) is one of the adjacent points of (2), the unwrap processing for the point is already performed and the processing state value 1 is given. However, in this instance the comparison with the reference point (2) is again performed and the following processing state value is given according to the comparison result.

(ii) when the processing state value of a comparison point is 1 or more than 1;

Already given value and the value determined by the present processing differ more than τ and, phase difference from the reference point <0.5π, . . . perform unwrapping: add +1 to the previous processing state value (condition 3)

The previous phase value and the phase value obtained by the present processing are the same or, phase difference from the reference point ≧0.5π, . . . prevent unwrapping: unchange the processing state value (condition 4)

In the present embodiment as illustrated, the results when point (2) is processed with reference to point (1) and when the point (1) is processed with reference to point (2) are the same, therefore, point (1) maintains the processing state value 1 as it is according to condition 4. As a result, the processing state map is given as shown in (d) of FIG. 9.

Now, it is assumed that when performing a comparison with the adjacent points using point (3) as a reference point, the processing state value of the right side adjacent point (6) performed with reference to the reference point (2) and that performed with reference to the reference point (3) differ more than π. In this instance, the condition 3 stands and the processing state value 2 is given, which implies that since the unwrap processing results in two directions differ, an indefiniteness with regard to the unwrapping is caused. Namely, when the unwrap processing state value takes more than 1, it is implied that an indefiniteness is caused in the unwrapping.

Figure 9:
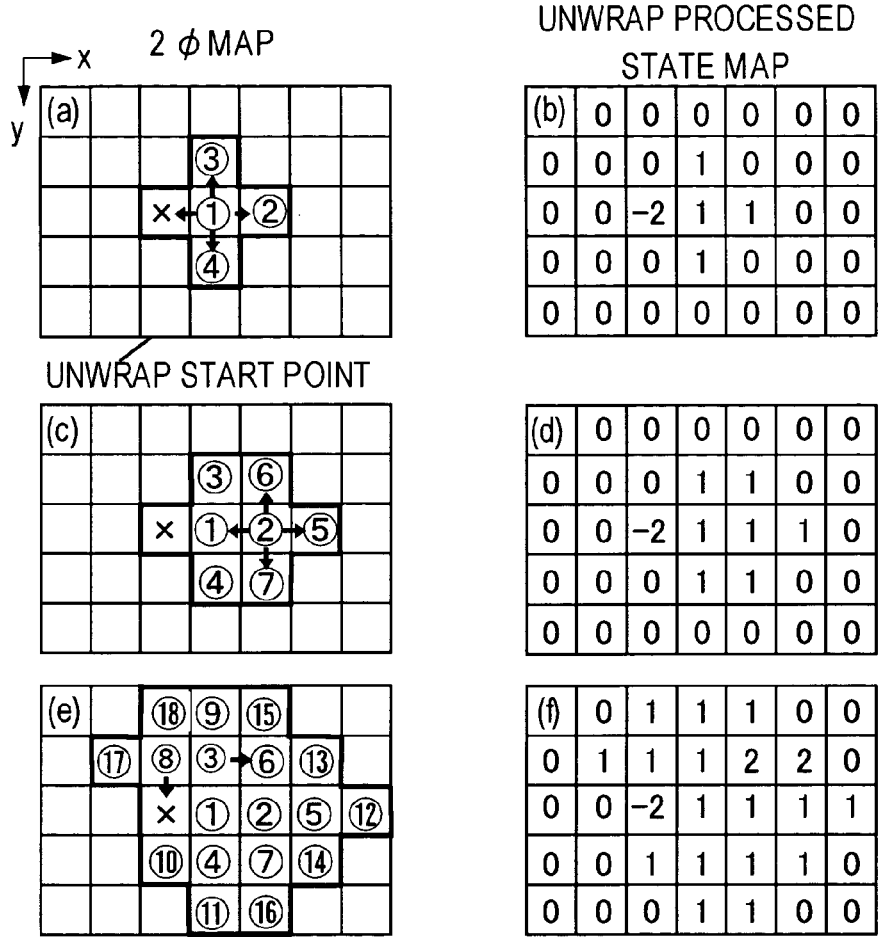
FIGS. 9(a) through (f) are diagrams for explaining a preparation method of an unwrap processing state map according to the present invention.

When the unwrap processing is further advanced while successively shifting the reference point and the processing is performed using point (8) as the reference point as shown in (e) of FIG. 9, the down side point marked by X assumes as a comparison point. The unwrap processing state value of the point marked by X is -2. In this instance, the processing is performed according to the following standard.

(iii) when the processing state value of the comparison point is -2;

Phase difference from the reference point<0.5π, . . . perform unwrapping: processing state value (condition 5)

Phase difference from the reference point≧0.5π, . . . perform unwrapping: unchange the processing state value (condition 6)

In this instance, the point marked by X is compared with the reference point (8), and if the condition 5 is satisfied, the point marked by X is assigned number 19 encircled, and the unwrap processing value 1 is given. On the other hand, if the condition 6 is satisfied, no processing is performed.

As has been explained hitherto, through continuing the same unwrap processing while shifting the reference point from smaller numbers successively the unwrap processing state map is obtained which gives one of the processing state values to all of the unwrap processing object pixels.

FIG. 8(*d*) shows in an image form thus prepared unwrap processing state map 804. In the drawing, circumferential black region and center black regions 8041 are non processing object regions, therefore, the unwrap processing state thereof is 1. A center gray region 8042 is a portion where the unwrap processing has already been completed and the unwrap processing state value thereof is 1. In this unwrap processing state map, regions indicated by white are regions having an unwrap processing state value more than 1. Namely, in FIG. 8(*a*) an upper vertical white line 8043 and three horizontal white lines 8044, 8045 and 8046 at right and left sides are the regions having a unwrap processing state value more than 1.

When observing the phase 2φ map (FIG. 8(*c*)) after unwrap of the above processing state, in the region 802 surrounded by the while line, the phase discontinues at the border of vertical white line 8043 in the unwrap processing state map 804. This is because, for example, the value unwrapped from an arrow (1) direction at the border 8043 is different from that unwrapped from an arrow (2) direction thereat.

When there are points having value more than 1 in the unwrap processing state map as has been referred to above, there exist protons where the phase therein is discontinuous even after the unwrap processing. Therefore, in the unwrap processing properness judgement step, when there are points having value more than 1 in the unwrap processing state map, it is understood that there are some errors during unwrapping and is judged that the unwrap processing was performed improperly. On the other hand, if unwrap processing state values for all of the pixels in the unwrap processing state map is less than 1, it is understood that the unwrapping has been performed properly and is judged that the unwrap processing is proper.

Figure 10:
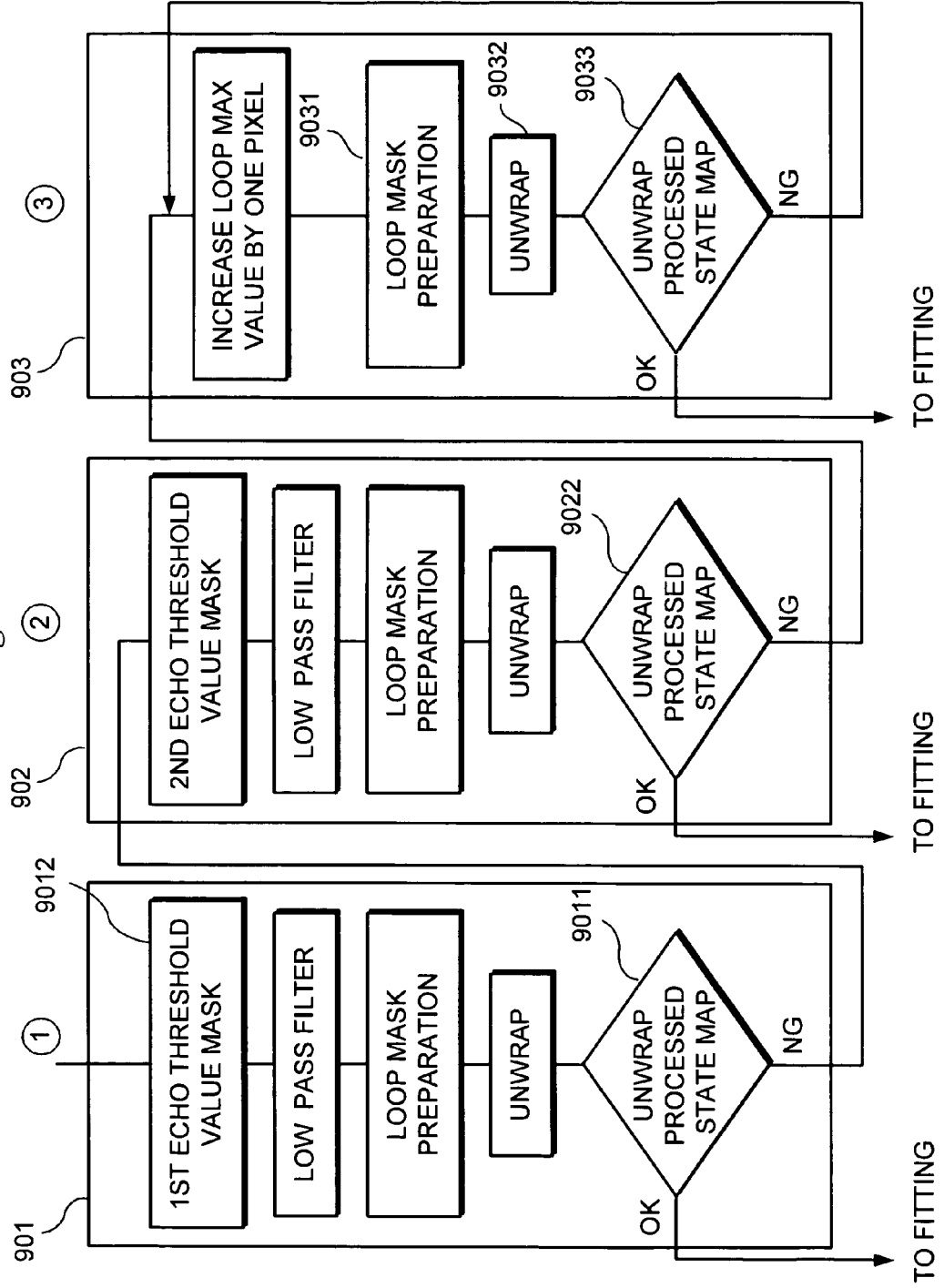
FIG. 10 is diagram showing an embodiment of an automatic unwrap processing flow according to the present invention.

According to the judgement result, when it is judged that the unwrapping was performed improperly, reprocessing is performed after altering the mask condition. As has been already explained, the mask condition alternation includes such as the addition of a new mask and alternation of the maximum value of one side in the loop mask. An example of the unwrap automation algorisms is shown in FIG. 10.

The automatic unwrap algorism includes processing 901 which uses the first echo threshold value mask, processing 902 which uses the second echo threshold value mask and processing 903 which varies the maximum value of the loop mask.

At first, a usual unwrap processing is performed in processing 901. Namely, through masking the phase 2φ map before unwrapping with the first echo threshold value mask noises on the phase 2φ map are removed, and further while applying a low pass filter (LPF), a loop mask is prepared. The maximum value of one side in the loop mask in this instance is set at a small value, for example, of about 2~3 pixels. Subsequently, while advancing the unwrap processing with region growing method, the unwrap processing state map is prepared.

After the unwrap processing, it is judge with the above judgement method whether the unwrapping has been performed properly with reference to the prepared unwrap processing state map (9011). If the judgement is OK, the process moves to the fitting, and if the judgement is NG, the process moves to a subsequent processing 902.

In the processing 902, the second echo threshold value mask 9021 is applied in addition to the previously applied first echo threshold value mask 9012 and the same processing as in the processing 901 is performed. Through the application of the second echo threshold value mask 9021 in this processing, noise contamination can be prevented in a region (W(x, y)~F(x, y)) in which the intensities of the water signal W(x, y) and the fat signal F(x, y) are substantially the same of which region exist between a region (W>F) where the water signal intensity W(x, y) is larger than the fat signal intensity F(x, Y) and a region (W<F) where the fat signal intensity is larger than the water signal intensity.

In step 9022 in this processing, it is also judged whether the unwrapping has been performed properly with reference to the unwrap processing state map, if the judgement is OK, the process moves to the fitting, and if the judgement is NG, the process moves to a subsequent processing 903.

In the processing 903, a loop mask is prepared by increasing the maximum value of one side in the loop mask (step 9031). Through the increasing of the maximum value of one side the mask is strengthened to thereby further remove unwrap error sources. If the maximum value of one side in the loop mask is set at a large value at the initial stage, the region of unwrap processing is hard to grow, because unnecessarily strong mask is applied and the accuracy of fitting of the phase 2ϕ map decreases which is performed later. Accordingly, the maximum value of one side in the loop mask is gradually increased (in this instance by one pixel) at the timing when unwrap processing error is caused, thereby, a proper unwrap processing is performed while keeping a maximum unwrap processing region.

Subsequently, after performing unwrap processing 9032, in step 9033 in this processing it is also judged whether the unwrapping has been performed properly with reference to the unwrap processing state map, if the judgement is OK, the process moves to the fitting, and if the judgement is NG, the process returns to the processing 903. The processing 903 is repeated until the unwrap processing state map becomes OK.

In the fitting module (FIG. 6, 606), a processing of estimating phases is performed for the regions where the masks are applied, thereby, no unwrap processing has been performed. For the phase value estimation any known function fitting methods can be employed. Since the phase 2ϕ map to be determined is in two dimension, the function fitting is performed with regard to two dimension.

A map obtained by the fitting can be used as it is as the phase 2ϕ map after fitting, however, after comparing the phase 2ϕ map after fitting with the phase 2ϕ map before fitting for every pixel, "a phase 2ϕ map after fitting" can be completed, by adding or subtracting only the most close 2nπ (n is a positive integer) with respect to the difference before and after fitting onto the phase 2ϕ map before fitting. Through effecting the above processing, a result which completely reflects all of the phase information before the fitting can be obtained. Namely, the water and fat image separation can be achieved in which even a phase offset due to local offset of the resonance frequency f0 caused by, for example, local noises and eddy current, factors other than the static magnetic field inhomogeneity is corrected. On the other hand, a phase 2ϕ map after fitting without the above processing is thought to reproduce a primary static magnetic field not containing noise influences.

Subsequently, by making use of a phase map obtained by the fitting module, herein the static magnetic field inhomogeneity map, the phase of the second echo is corrected according to the following equation;

$$S2'(x,y)=S2(x,y)\exp(-i\phi(X,y)) \qquad (10)$$

wherein S2'(x, y) is the second echo of which phase is corrected.

With the above equation the phase offset of the second echo which is caused by the static magnetic field inhomogeneity during the lapsed time τ from the first echo generation is corrected. Thereby, with the following equations (11) and (12), an addition image corresponding to a water image and a subtraction image corresponding to a fat image can be obtained respectively;

$$S1(x,y)+S2'(x,y)=2W(x,y)\exp(i\alpha(x,y)) \qquad (11)$$

$$S1(x,y)-S2'(x,y)=2F(x,y)\exp(i\alpha(x,y)) \qquad (12)$$

In this instance, when assuming the phase calculation is correct, an addition image corresponding to a water image and a subtraction image corresponding to a fat image are in principle obtained, however, in practice since it is possible during unwrapping of the phase 2ϕ map that a phase offset of 2nπ is superposed, the determination of water and fat images can be reversed. Namely, an addition image corresponding to a fat image and a subtraction image corresponding to a water image can be obtained.

Although these phase offsets can be prevented by adding a processing of varying an unwrap starting point, however, in the above explained region growing method, since the unwrap processing starting point is automatically determined in order to permit the unwrap processing to be performed in a broad area, it is preferable to perform a phase matching processing after the unwrap processing.

Figure 11:
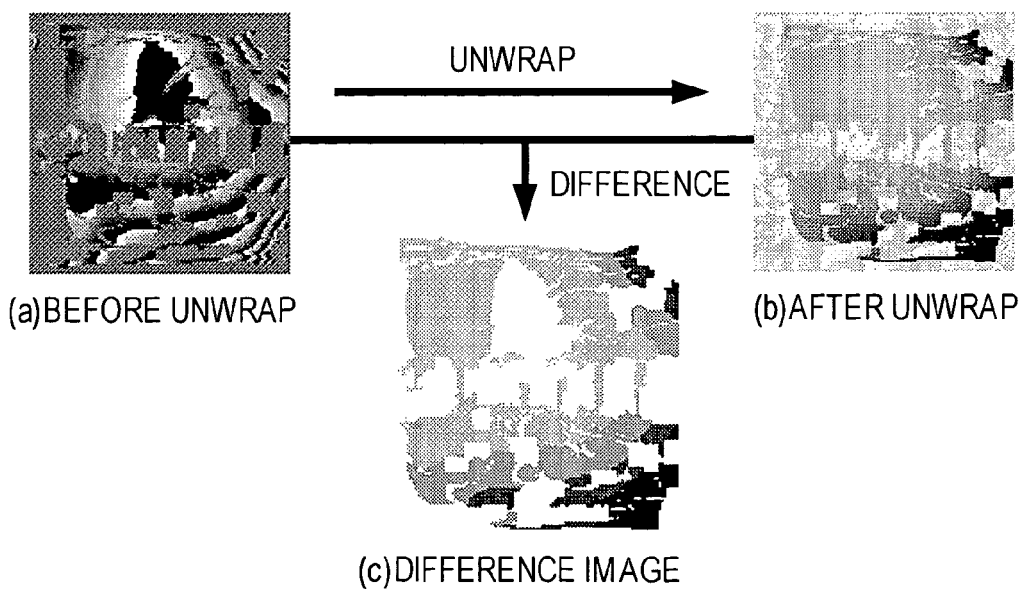
FIGS. 11(a) through (c) are diagrams showing in image forms a phase aligning state after unwrap processing according to the present invention.

Such phase matching algorism is shown in FIG. 11. In this processing, 2ϕ map before unwrap (a), 2ϕ map after unwrap (b) and difference therebetween (c) are used. Because of the nature of the unwrap the respective values on the difference (c) take 2nπ to show a distribution of n. Then, the phase values of all pixels are shifted by ±2mπ (m=0, 1, 2, . . . ) so that the phase values of 2ϕ maps before and after unwrap on a region of n which appears most frequently in the above distribution become equal. This is based on an assumption that the region of n which appears most frequently will greatly contribute for deciding the resonance frequency f0 during data imaging.

Through adding such phase matching processing, a certainty of obtaining a water image in a form of an addition image and a fat image in a form of a subtraction image can be enhanced. However, even with the phase matching method it is possible that the water and fat images can not be obtained correctly, in such instance, it is preferable to employ another automatic discrimination method between water and fat images as will be explained later.

According to FIG. 10 embodiment as the mask for the unwrap processing a stepwise combination of the first echo threshold value mask, the second echo threshold value mask and the loop mask while varying the conditions thereof is used as well as in parallel with the advancement of the unwrap processing the unwrap processing state map is prepared to judge whether or not the unwrap processing is performed properly, thereby, a proper unwrap processing can be performed without unnecessarily strengthening the mask.

Now, another embodiment of the phase 2ϕ map preparation module according to the present invention will be explained. In the present embodiment, in place of the second echo threshold value mask in FIG. 10 embodiment a mask making use of (second echo signal)/(first echo signal) (hereinbelow will be referred to as ec2/ec1 mask) is used.

Figure 12:
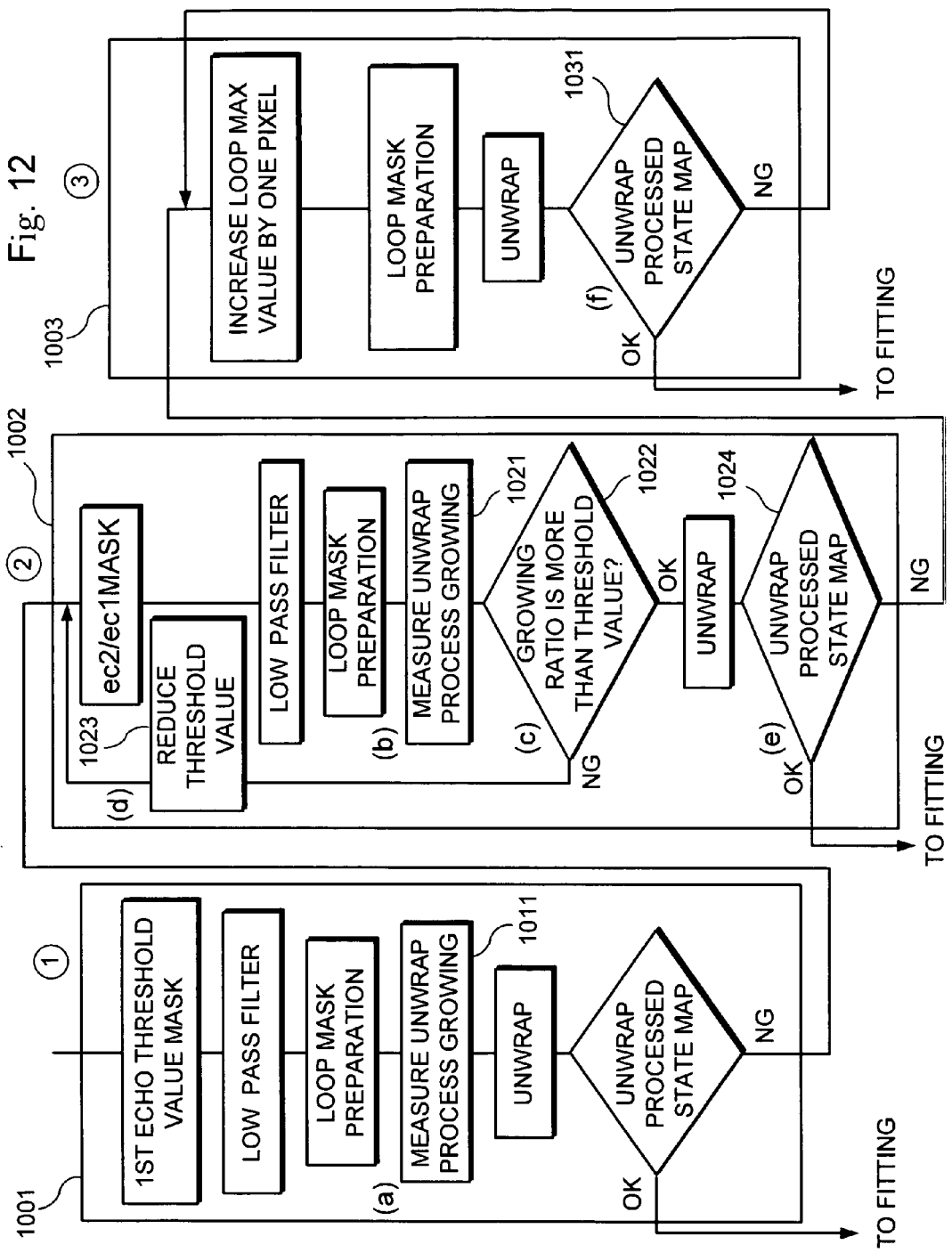
FIG. 12 is a diagram showing another embodiment of an automatic unwrap processing flow according to the present invention.

FIG. 12 shows the unwrap automation algorism according to the present embodiment and the present unwrap automation algorism includes a processing 1001 which makes use of the first echo threshold value mask, a processing 1002 which makes use of a ec2/ec1 mask and a processing 1003 which varies the maximum value of the loop mask.

The ec2/ec1 mask is a mask which determines the value (second echo signal)/(first echo signal) and gives 1 when the determined value is more than a predetermined threshold value and gives 0 when the determined value is less than the predetermined threshold value, and is introduced to remove a phase disturbance at the border between the region (W>F) where the water signal intensity W(x, y) is larger than the fat signal intensity F(x, y) and the region (W<F) where the fat signal intensity is larger than the water signal intensity.

According to the study of the present inventors, it was confirmed that these special phase disturbances are caused by the computation which doubles the phase determined from the first echo and the second echo and are induced by (i) existence of static magnetic field inhomogeneity and (ii) gradual variation from W>F to W<F. Therefore, when the value of (second echo signal)/(first echo signal) is less than the threshold value, through masking the concerned pixel such phase disturbance is removed.

More specifically, a ratio of the absolute values of the first echo image and the second echo image is determined and a mask is applied to a region where the determined ratio is less than a threshold value mt according to the following in-equation (13).

$$|We^{-TE2/T2^*W} - Fe^{-TE2/T2^*F}|/|We^{-TE1/T2^*W} + Fe^{-TE1/T2^*F}| < mt \quad (13)$$

In the above in-equation, TE1 and TE2 are respectively TE of the first echo and the second echo, and T2*W and T2*F are respectively T2* of water and fat. From in-equation (13), it will be understood that the present ec2/ec1 mask is sensitive at the border between the region of W>F and the region of W<F in comparison with the second echo threshold value mask.

Now, the processing by the unwrap automation algorism as shown in FIG. 12 will be explained. At first in the processing 1001 the unwrap processing is performed by making use of the first echo threshold value mask. Although the processing 1001 is substantially the same as the processing 901 in FIG. 10, in the present embodiment a processing 1011 which checks before unwrapping how the region grows is added. The region growing measured by the present processing is compared with a region growing measured by a similar processing 1021 in the processing 1002 which will be explained later, and which is used for adjusting the intensity of the ec2/ec1 mask.

In this first processing 1001 like the previous embodiment the unwrap processing state map is prepared in parallel with the unwrap processing, and it is judged whether each processing state value of all pixels on the map is less or more than 1 and the properness of the unwrap processing is judged. When it is judged that the unwrap processing has been performed properly, the process moves to the fitting module.

When it is judged that the unwrap processing is NG, the process moves to the processing 1002 wherein the ec2/ec1 mask is applied to the phase 2φ map after the processing 1001. More specifically, a mask which removes pixels satisfying the following in-equation (14) using the threshold value mt is applied.

Absolute value of second echo signal/Absolute value of first echo signal<mt    (14)

With this measure, as has been already explained, the portion where the phase disturbance was caused at the border between the region (W>F) and the region (W<F) can be removed from the unwrap processing. Subsequently, after passing the low pass filter and preparing the loop mask, the growing of the unwrap processing is measured (step 1021), and it is judged whether the growing of the unwrap processing is sufficient (step 1022). The judgement is performed through comparison of the result at step 1011 in the processing 1001 with the result at step 1021 in the processing 1002.

Figure 13A:
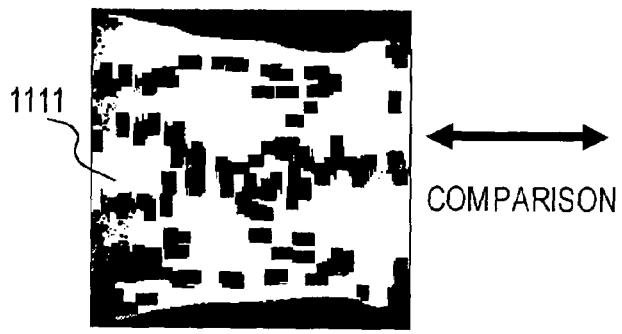
FIGS. 13(a) and (b) are diagrams showing in image forms of measurement of a growing unwrap processing in the processing flow as shown in FIG. 12.
Figure 13B:

FIG. 13 shows in image forms the result of measurement of the unwrap processing growing, and (a) in FIG. 13 is the result at the growing measurement step 1011 in the processing 1001 which makes use of the first echo threshold value mask and (b) in FIG. 13 is the result of the growing measurement step 1021 in the processing 1002 which makes use of the ec2/ec1 mask. Herein, regions 1111 and 1121 indicated in white are the growing regions of the unwrap processing and at the respective growing measurement steps 1011 and 1021 in the processings 1001 and 1002 areas (number of pixels) of the respective regions 1111 and 1121 as indicated in white are determined.

At step 1022, a ratio R of the areas of the regions respectively determined in these steps 1011 and 1021 is determined. When the ratio R satisfies R≧a predetermined value (for example, 0.8), it is judged that the unwrap region will sufficiently grow and the process moves to the unwrap processing. On the other hand, when R<0.8, it is judged that the growing of unwrap region is insufficient, the process moves to step 1023 where the threshold value mt of the ec2/ec1 mask is reduced and the processing is again respected. Such processing is repeated until R≧0.8 is satisfied.

After performing the unwrapping while adjusting the threshold value mt of the ec2/ec1 mask in the above manner, the unwrap processing state map which was prepared in the step 1024 is referred to. In the present embodiment like the processing 1001, it may be judged whether each processing state value of all pixels is less or more than 1, or alternatively the judgement can be modified to permit pixels having the unwrap processing state value more than 1 if the same locate in a FOV peripheral region.

More specifically, when the threshold value mt of the ec2/ec1 mask which was adjusted previously reduces below mt2, the following processing which permits uncertainty of unwrapping is added.

Threshold value of ec2/ec1 mask≧mt2: not permit erroneous unwrapping,

Threshold value of ec2/ec1 mask<mt2: permit even if erroneous unwrapping remains at boundary of image.

The image of the threshold value of ec2/ec1 mask<mt2 implies one of which unwrap processing growing is weak from the outset, therefore, if the maximum value of one side of the loop mask is increased for such images, the growing of the unwrap processing suddenly reduces and the result of fitting which is performed successively may become improper. Accordingly, in such instance, through allowing such pixels even if erroneous unwrapping remains at the image periphery, an excessive strengthening of the loop mask is prevented.

Figure 14:
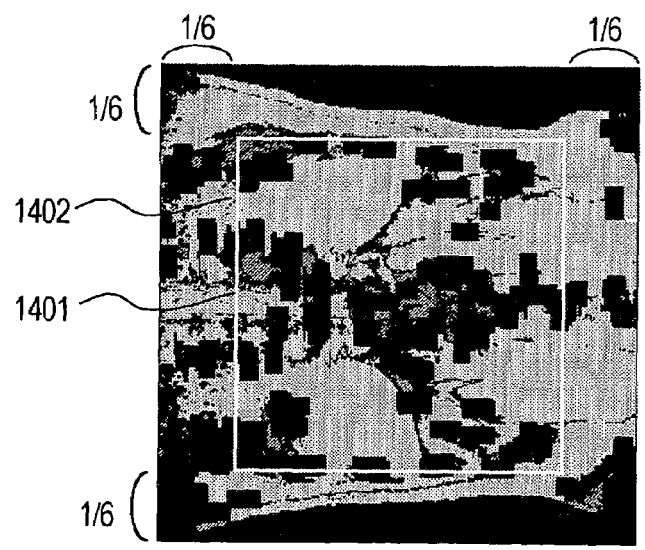
FIG. 14 is a diagram for explaining in an image form of one step in an unwrap properness judgement processing according to the present invention.

FIG. 14 shows a range where such erroneous unwrapping is permitted. Namely, a FOV peripheral region (⅙ area from the outer edge of FOV) 1402 outside a white rectangular 1401 in FIG. 14 is permitted even if an unwrap uncertainty exists.

Even after performing such comparatively loose unwrap processing state judgement, when the unwrapping is NG, the process advances to the subsequent processing 1003. The processing 1003 is the same as the processing 903, in that the unwrap processing is performed while varying the maximum value of one side of the loop mask. Herein, in step 1031 in which properness of the unwrap processing is judged, like the processing 1002 which makes use of the ec2/ec1 mask the processing which permits unwrapping for the region of FOV periphery can be added, even if there exists uncertainty therein. Thereby, a growing limitation of unwrap region due to excessive strengthening of the loop mask can be prevented. Likely, in this instance it is understood that such a loose judgement does not lead to deterioration of diagnosis information represented by a final image.

As has been explained above, through advancing the processings 1001, 1002 and 1003, the phase map after unwrap processing is obtained. The phase of the second echo is corrected by making use of the obtained static magnetic field inhomogeneity map obtained after fitting the phase map, and through addition and subtraction of the phase corrected second echo and the first echo a water image and a fat image are obtained, which is the same as the data processing flow as shown in FIG. 5.

Likely in the present embodiment, the phase matching processing can be added which removes the phase offset by comparing of the phase before processing with that after unwrap processing. In addition to the static magnetic field correction, a processing of adding or subtracting only the most close 2nπ (n is a positive integer) with respect to the difference before and after fitting onto the phase 2φ map before fitting can be added after the fitting, thereby, the water and fat separation can be achieved in which even a phase offset due to local offset of the resonance frequency f0 caused by, for example, local noises and eddy current is corrected.

According to FIG. 12 embodiment, since the ec2/ec1 mask which is sensitive at the boundary between the region W>F and the region W<F is employed as the mask for the unwrap processing, influences affecting the unwrap processing of the phase disturbance caused at the boundary are eliminated. Further, according to the present embodiment since the function of checking growing of the unwrap processing is added between the processing by means of the first echo threshold value mask and the processing by means of the ec2/ec1 mask, the intensity of the mask can be adjusted. Still further, with regard to the properness judgement of the unwrap processing state, since the judgement standard at the peripheral region is loosened, an excessive strengthening of the loop map as well as an excessive elongation of the processing time can be prevented.

Figure 15:
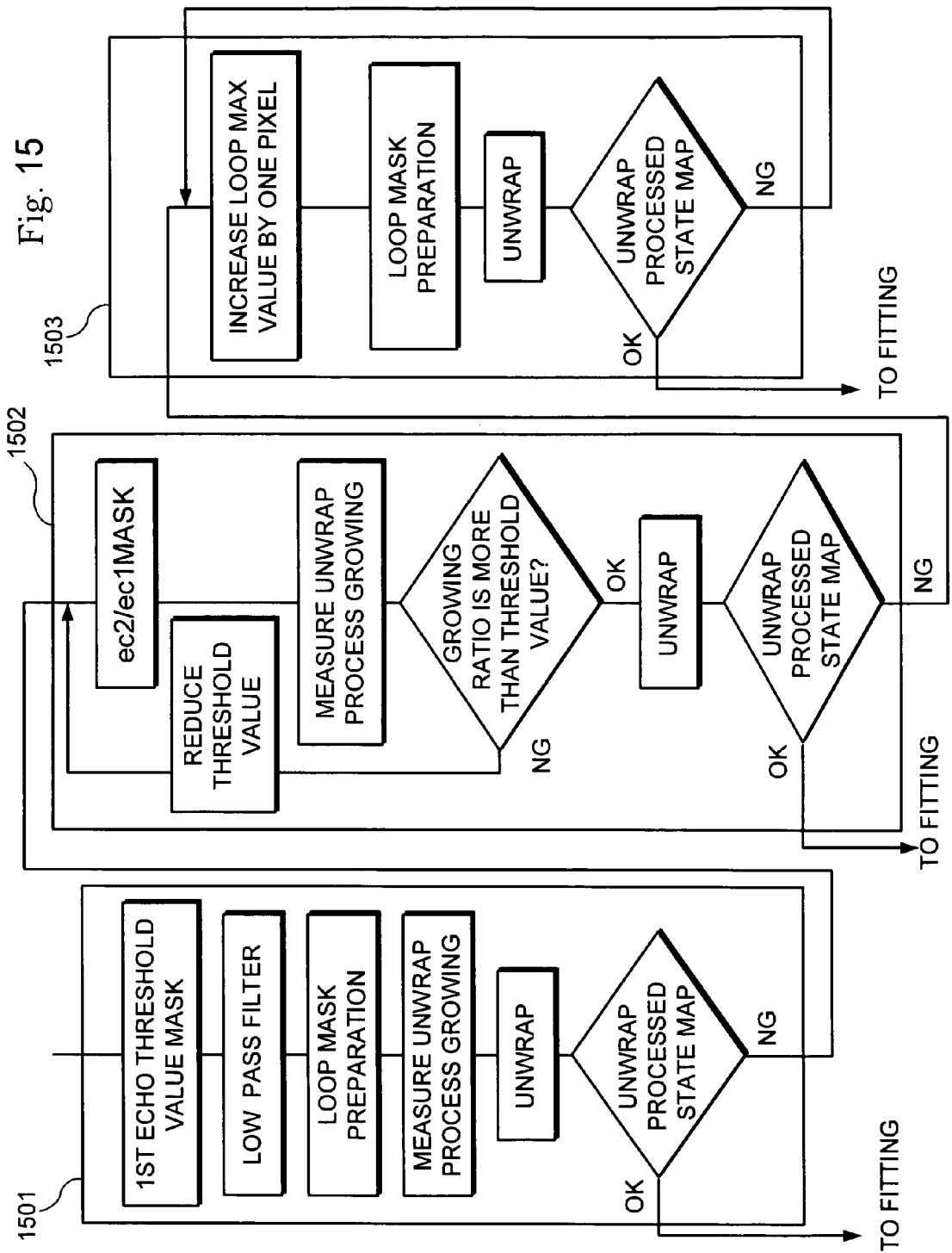
FIG. 15 is a diagram showing still another embodiment of an automatic unwrap processing flow according to the present invention.

Now, still another embodiment of the phase map preparation module according to the present invention will be explained. The present embodiment simplifies the module itself and shortens the unwrap processing time by locating a part of the processing outside the processing loop. The processing flow of the present embodiment is shown in FIG. 15.

Among the present processing flow, a processing 1501 which makes use of the first echo threshold value mask and a processing 1503 which alters the maximum value of one side of the loop mask are the same as the processings 1001 and 1003 in FIG. 12, however, in a processing 1502 which makes use of the ec2/ec1 mask the low pass filter processing and the loop mask preparation processing are omitted from the processing loop which alters the threshold value of the ec2/ec1 mask until the ratio of unwrap processing growing becomes more than the threshold value to shorten the loop processing time. The simplification of the processing is not limited to the present embodiment, but can be applied to other embodiments.

Further, as a further embodiment which shortens the processing time, it is possible to reduce the matrix size when preparing phase 2φ map.

In this instance, at the first stage of the phase 2φ map preparation a module is added which reduces the respective matrix sizes of the first echo image and the second echo image, thereafter, the 2φ map preparation is performed with respect to the reduced size images. The prepared 2φ map after fitting is restored to the original matrix size (step 1602), thereafter, the separation processing between water and fat is performed.

Figure 17:
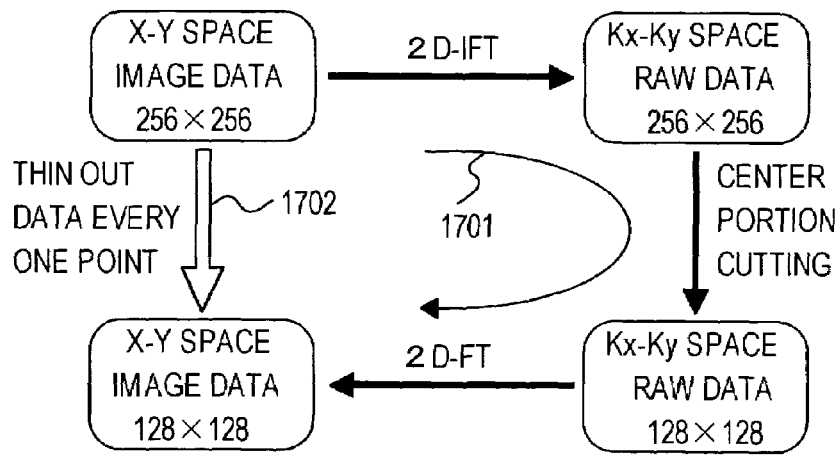
FIG. 17 is a diagram for explaining the matrix reducing method as shown in FIG. 16.

FIG. 17 shows a method of reducing matrix size. In the drawing, with the method shown by 1701 at first image data in actual space are converted through Inverted Fourier Transformation (2D-IFT) to data in Kx-Ky space, after cutting out a portion of the data, the data are converted through Fourier Transformation to an image in actual space. Further, with the method shown by 1702 the data are simply thinned-out, for example, for every one point. With this method, some image quality deterioration can be caused, however, the time consumed for the Fourier Transformation can be reduced by the time corresponding to the transformation time of four times in maximum.

Figure 2:
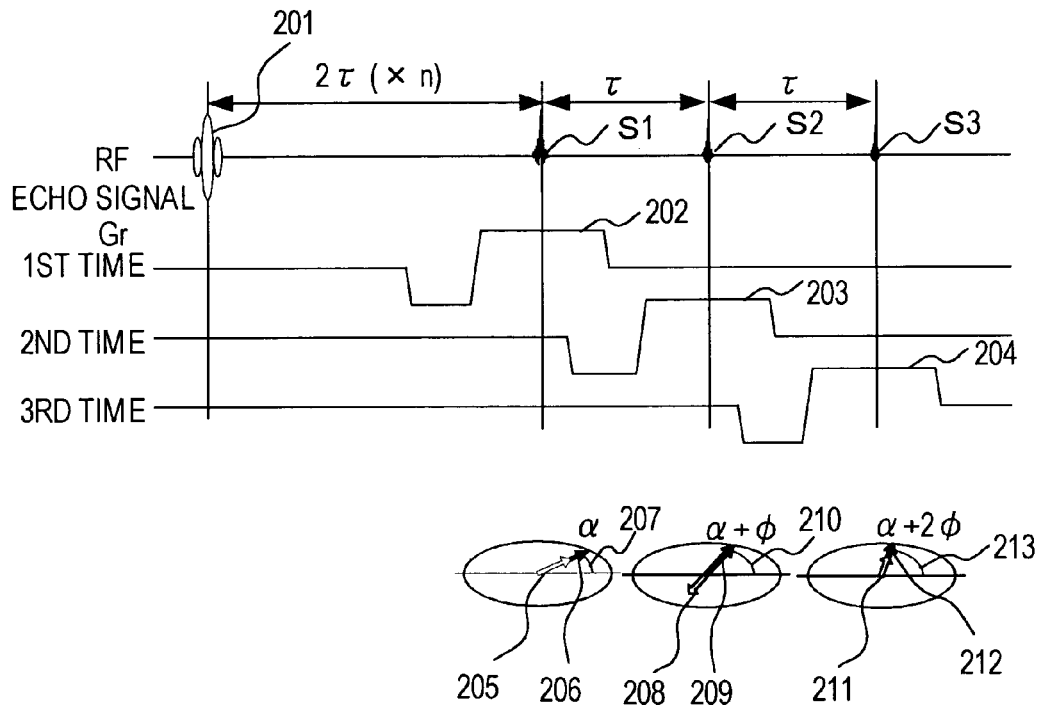
FIG. 2 is a time chart of data acquisition in a 3-point Dixon method.

Hereinabove, the methods have been explained in which from two types of signals having different echo times TE obtained by the pulse sequence based on the 2-point Dixon method the static magnetic field inhomogeneity map is prepared, in this instance the automatic algorism processing for the unwrap processing is performed and separated water and fat images are obtained after correcting the phase of the signals, however, the automation algorism for the unwrap processing according to the present invention is not limited to the 2-point Dixon method, but can be applied to an instance in which three types of signals having different echo times are successively measured as shown in FIG. 2 and a static magnetic field inhomogeneity distribution is determined through computation between the three types of signals.

Hereinbelow, a method of determining a static magnetic field inhomogeneity distribution according to a 3-point Dixon method will be explained briefly. At first as shown in FIG. 2, image taking of three times while varying TE is performed to obtain three signals S1, S2 and S3. TE of the first echo S1 is set at an integer multiple of 2π, and TE of the second echo S2 is set longer by τ from TE of the first echo S1 and TE of the third echo S3 is set further longer by τ from TE of the second echo.

At the time when the first echo is measured, the water signal 206 and the fat signal 205 are in in-phase and have a phase 207 of which value is assumed as α. At the time when the second echo is measured, the water signal 209 and the fat signal 208 are in anti-phase, and the phase of the water signal at this moment assumes α+φ. φ represents a phase rotation amount due to static magnetic field inhomogeneity. At the time when the third echo is measured, the water signal 211 are again in in-phase and of which phase value is α+2φ. Since the water signals and the fat signals in the first and second echoes are in in-phase, through determination of the phase S3(x, y)/S1(x, y) a phase rotation amount due to the static magnetic field inhomogeneity can be determined. Namely, $$S1(x,y)=(W(x,y)+F(x,y))\exp(i(\alpha(x,y)))$$

$$S3(x,y)=(W(x,y)+F(x,y))\exp(i(\alpha(x,y)+2\phi(x,y)))$$

$$\arg(S3(x,y)/S1(x,y))=2\phi(x,y)$$

wherein arg ( ) implies to determine phase.

Figure 16:
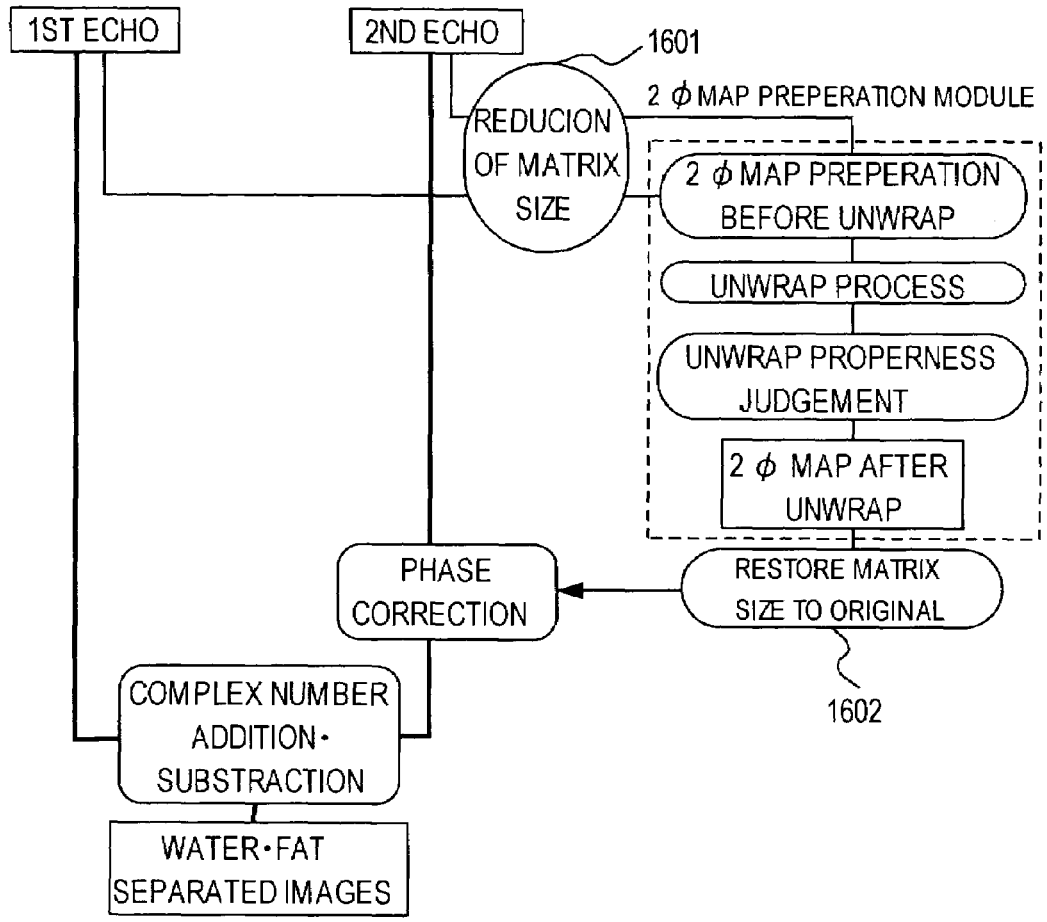
FIG. 16 is a diagram showing a flow in which a matrix reducing step is introduced in to a processing flow of the Dixon method with static magnetic field correction as shown in FIG. 5.

A phase map in which 2φ(x, y) is determined for all of (x, y) is subjected to an unwrap processing according to the data processing flow in FIG. 5 or FIG. 16 and FIG. 6, then the result is divided by 2 to obtain phase rotation amount φ(x, y) due to static magnetic field inhomogeneity. By making use of the obtained φ(x, y), the phase correction of the signal S2 is performed, the addition image and the subtraction image are obtained in the same manner as in the 2-point Dixon method.

Figure 18A:
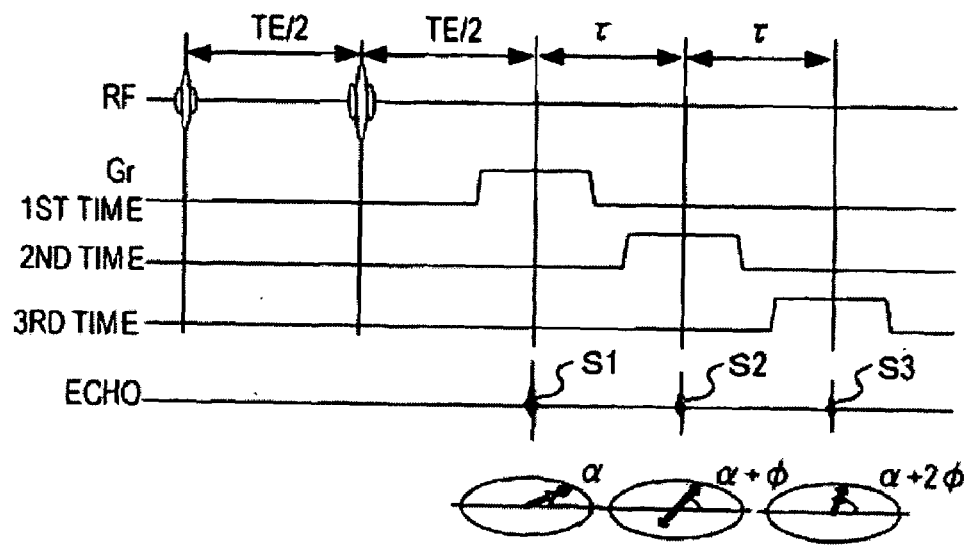
FIGS. 18(a) and (b) are time charts for data acquisition with a 3-point Dixon method which is employed in the present invention.
Figure 18B:
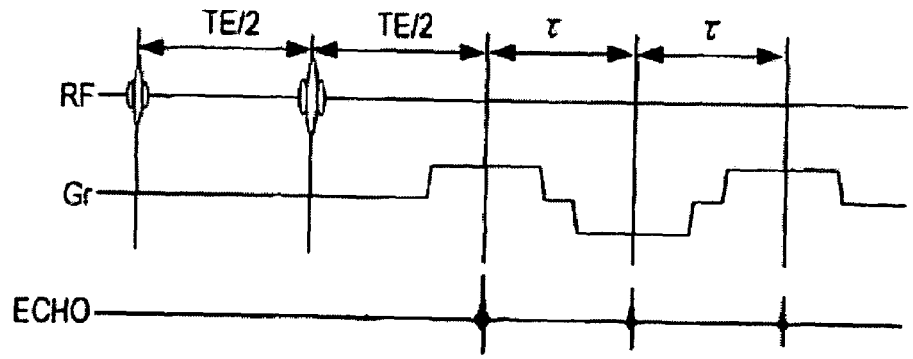

Further, in FIG. 2, an example in which signals having different echo times are obtained by three time measurements was illustrated, however, it is possible to obtain three signals having different echo times within a single repetition time. Further, in the present embodiment a sequence of gradient echo method was exemplified, however, a sequence of spin echo method as shown in FIGS. 18(*a*) and 18(*b*) can also be employed.

Further, in the above embodiment, the application of 0° and −180° two echo sequence is exemplified, however, an application of 0° and −90° two echo sequence is possible after adding necessary modification to the former, in this instance, 2φ map is modified to 4φ map.

Further, other than for obtaining the separated water and fat images, the present automation algorism for the unwrap processing can be applied generally to an MRI device having a function of determining a phase map such as static magnetic field inhomogeneity map. The above automation algorism for the unwrap processing, for example, can also be used for an MRI device provided with an auto slimming function which, after obtaining a static magnetic field inhomogeneity map, drives sim coils so as to generates magnetic field having the same magnitude but of opposite polarity thereto, and an MRI device which permits phase correction with regard to such as distortion and position offset in images obtained by sequences susceptible to static magnetic field inhomogeneity such as EPI (Echo Planar Imaging) method.

Now, as a second aspect of the present invention, a method of automatically discriminating a water image and a fat image from an addition image and a subtraction image in the water and fat separated image taking will be explained.

As has been explained previously, with the Dixon method, if the phase computation is correct, a water image in a form of addition image and a fat image in a form of subtraction image are in principle obtained, however, in practice such is sometimes reversed and further such can be caused even when a phase matching is performed after unwrap processing. Namely, in connection with the unwrap processing of the phase 2φ map uncertainty of 2nπ always exists.

In the automatic discrimination method according to the present invention, under a precondition of the above referred to uncertainty in association with the unwrap processing, a method of automatically discriminating two types of images obtained through computation is provided. For this purpose, two discrimination methods are employed. (1) A method of comparing ratios of pixel values of the first echo image and the second echo image, in that the signal ratios, and (2) a method of directly comparing pixel values of the addition and subtraction images. These methods will be explained in detail hereinbelow.

(1) The method of comparing ratios of pixel values of the first echo image and the second echo image is based on an assumption that with regard to the ratio of [pixel value of the second echo image]/[pixel value of the first echo image] (hereinafter will be referred to as signal ratio), the water signal shows a larger value. Namely, since T2 value of water signal is longer in comparison with that of the fat signal, the signal attenuation thereof between the first echo image and the second echo image is weak, therefore, the signal ratio thereof gives a larger value. Strictly speaking, the signal attenuation between the first echo image and the second echo image is T2* attenuation, because the influence such as due to the static magnetic field inhomogeneity is included, however, difference of the signal ratios of the water signal and the fat signal is held unchanged. Therefore, in the present discrimination method, the above fact is made use of.

Figure 19:
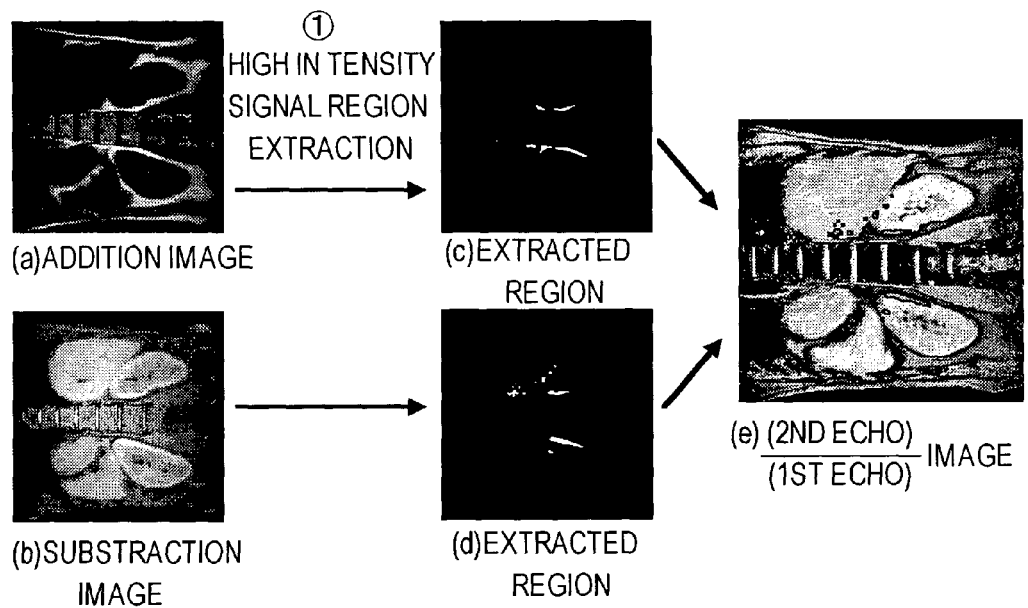
FIGS. 19(a) through (e) are diagrams for explaining in image forms an example of an automatic discrimination algorism of water and fat images according to the present invention.

FIG. 19 shows an algorism for deciding between a water image and a fat image according to the signal ratios. At first with regard to the addition image (a) and the subtraction image (b) high intensity signal regions are respectively extracted as high pixel value regions (c) and (d). In this instance, it is preferable that number of pixels in the region extracted is about 1% in the region having signals (namely, pixel number on the inspection subject region).

On the other hand, a signal ratio of the first and second echo images for every pixel on the inspection subject region is determined. On the thus determined signal ratio image the high pixel value regions (c) and (d) which are formed by extracting a high intensity signal region are superposed to form an image (e), and an average value of the signal ratios on the portion where the high pixel value region (c) of the addition image is superposed is compared with an average value of the signal ratios on the portion where the high pixel value region (d) of the subtraction image is superposed.

Since the signal ratio of the water signal is presumed larger as has been explained above, as the result of the above comparison, the image having a larger value of signal ratio is judged as the water image. Namely, among the signal ratios of the addition image extraction region and of the subtraction image extraction region, one having a larger value is judged as the water image and one having a smaller value is judged as the fat image.

In case of the 3-point Dixon method, by plotting the pixel values of the first, second and third echo images in an exponential function, attenuation coefficients can be obtained, and one having a larger attenuation coefficient is judged as the fat image.

The accuracy of the above method can be further enhanced, when the following condition is added in which when a difference (or ratio) between the signal ratio of the addition image extraction region and the ratio of the subtraction image extraction region is more than a predetermined value, one having a larger value of signal ratio is judged as the water image.

In actual measurement, with regard to some tissue in which water protons exist, T2 thereof is shorter than that of bulk phase water and comes close to that of the fat signal, as a result, a measurement error can be caused. For example, at the portions such as ankle and knee, a muscle as a region showing a high water signal and subcutaneous fat as a region showing a high fat signal are extracted, however, since the molecules existing in the muscle couple with proteins, T2 thereof is shorter than of bulk phase water. Therefore, it is understood that the signal ratio of the water signal comes close to the signal ratio of the subcutaneous fat signal which makes their discrimination difficult.

Therefore, among the signal ratio of the addition image extraction region and the signal ratio of the subtraction image extraction region as has been explained above, only when a ratio of the "larger signal ratio" to the "smaller signal ratio" is more than a threshold value m (>1), a processing is performed to determine the "larger signal ratio" of the extraction region as the water image and the "smaller signal ratio" thereof as the fat image. Thereby, portions including errors are removed and the accuracy of judgement can be enhanced. The value of the above threshold m is not limited, however, according to the study of the inventors it is understood that m=1.2 or therearound is preferable.

However, when adding the above condition, if the ratio of the "larger signal ratio" to the "smaller signal ratio" satisfies the following inequation, the water and fat images can not be determined with the addition and subtraction images;

$$1 \leq [\text{larger signal ratio}]/[\text{smaller signal ratio}] \leq m$$

Accordingly, the automatic discrimination method of the present invention uses in parallel the method (2) in which the pixel values of the addition and subtraction images are directly compared as a second method.

The method of directly comparing the pixel values of the addition and subtraction images makes use of the fact that the maximum pixel value of the fat image is larger than the maximum pixel value of the water image under a predetermined contrast determined by an image taking method employed or the opposite relation thereof. For example, in the spin echo (SE) sequence a T1 emphasized image is generally taken, therefore, under the contrast in such instance the maximum pixel value of the fat image is larger than the maximum pixel value of the water image. Therefore, in the present embodiment the water and fat images are discriminated by making use of the above feature.

Figure 20:
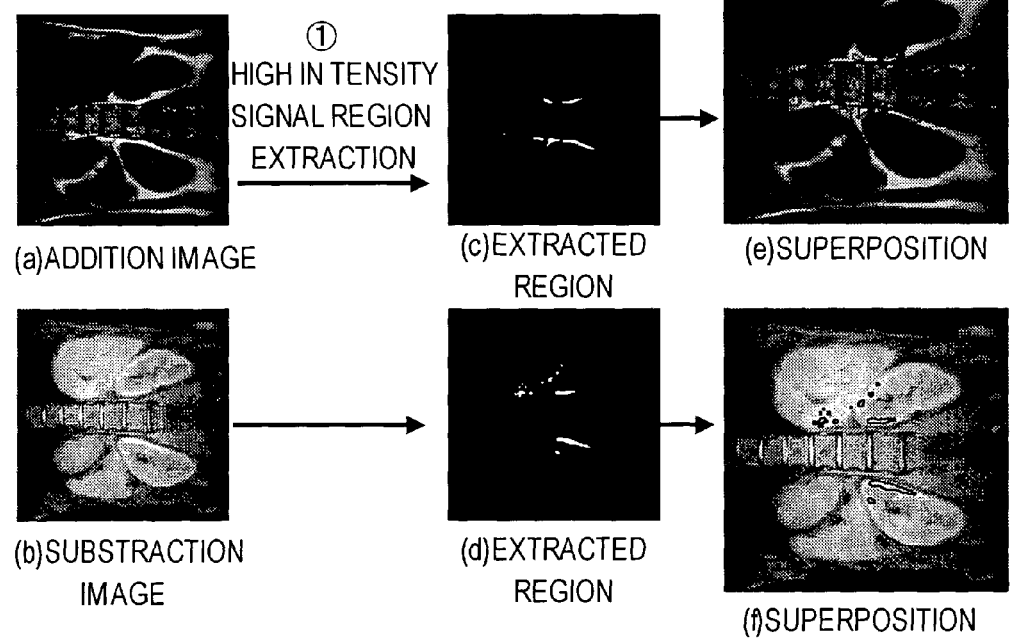
FIGS. 20(a) through (f) are diagrams for explaining in image forms another example of an automatic discrimination algorism of water and fat images according to the present invention.

FIG. 20 shows an algorism for realizing the above method (2). Likely, in this method at first from an addition image (a) and a subtraction image (b) high pixel value regions (c) and (d) are extracted. Subsequently, averages of pixel values of the images (a) and (b) with respect to the respective extracted regions are determined. (e) and (f) in FIG. 20 show images in which the images (a) and (b) are respectively superposed over the extracted images (c) and (d) in order to determine the pixel values with respect to the extracted regions. Thereafter, the average values of the determined pixel values are compared.

As has been explained above, under the contrast of T1 emphasized image, the average value of the fat pixel values is larger than the average value of the water pixel values, namely, it is expected to satisfies the following inequation;

(average of fat pixel values)/(average of water pixel values)>1

Accordingly, among the addition image and the subtraction image, the image having the larger average pixel value is judged as the fat image and the image having the smaller average pixel value is judged as the water image.

With this method, likely the judgement accuracy can be enhanced by eliminating a measurement error possibly caused during actual measurement. For this purpose, among the addition image and the subtraction image, a ratio between the "image having a larger average pixel value" and the "image having a smaller average pixel value" is taken and when the ratio shows to be larger than a predetermined threshold value p(>1), the image having a larger average pixel value is judged as the fat image and the image having a smaller average pixel value is judged as the water image.

Likely, in this embodiment, when the ratio [image having larger average pixel value]/[image having smaller average pixel value] satisfies the following inequation;

$1 \leq$ [image having larger average pixel value]/[image having smaller average pixel value]$\leq p$ the water and fat images can not be judged from the addition and subtraction images in the above manner, however, if the present method is used in parallel with the above method (1), the water and fat images can be discriminated.

Further, in the method (2) when the first echo image and the second echo image have other contrast than that of T1, the method can be applied in the same manner by varying the threshold values m and p.

When applying both methods, both methods can be applied in such a manner that one of the methods is used first and if the judgement can not be made with the method, then the other method is used.

After performing the discrimination as above, an indication as "water image" or "fat image" is applied on the image displayed. With the above method, since an automatic image discrimination can be performed even for tissues in which a tissue containing water and a tissue containing fat are interlaced in complex, a diagnosis of an inspection subject can be performed efficiently.

Automatic discrimination methods between water and fat images have been explained hitherto. The application of the present automatic discrimination method is not limited to the Dixon method, but the present method can be applied to a general method in which water and fat images are determined through computation of MR signals obtained at different echo times. In such instance, applicable image taking sequence is not only the sequence in which two echoes are obtained by a single excitation, but also a single scan sequence such as echo planar imaging (EPI) method and fast spin echo (FSE) method in which echoes necessary for one sheet image are obtained by a single excitation. In such instance, image taking time is further shortened.

In the above embodiments, the separation of water and fat is exemplified, however, if the image taking method relates to obtain two types of spin signals by making use of the chemical shift, the present invention is applicable to other combinations of materials, for example, with regard to separation of water and silicon, and water and NAA.

According to the present invention, when preparing a phase offset map due to such as a static magnetic field inhomogeneity by making use of plural signals having different echo times, an algorism which optimizes an unwrap processing is provided. Through applying such algorism to a water and fat separated image acquiring method such as Dixon method with static magnetic field correction, the water and fat separated images can be acquired in fully automatic.

Further, according to the present invention, in the method in which water and fat separated images are acquired through computation between plural signals having different echo times, a method which automatically discriminate either an addition image or a subtraction images as a water image or a fat image is provided. Through applying such method to a water and fat separated image acquiring method such as Dixon method with static magnetic field correction, the water and fat images can be drawn in fully automatic.

The invention claimed is:

1. A magnetic resonance imaging device which is provided with a magnetic field generation means which respectively generates a high frequency magnetic field and a gradient magnetic field in a space where a static magnetic field is formed, a signal processing means which detects a nuclear magnetic resonance signal generated from an inspection subject placed in the space and reconstructs an image therefrom and a display means which displays the reconstructed image, wherein the signal processing means performs, by making use of at least two nuclear magnetic resonance signals having different times TE from irradiation of the high frequency magnetic field signal to generation of the nuclear magnetic resonance signals, a computation determining a phase offset distribution between the generated nuclear magnetic resonance signals, and wherein the signal processing means performs an unwrap processing in which an unwrap processing state map is generated and a principal value of rotation caused in the computation determining the phase offset distribution is corrected, and at the same time, performs a judgement as to whether the unwrap processing is proper based on a consistency of values of a same point obtained by the unwrap processing in at least two different directions of the unwrap processing state map.

2. A magnetic resonance imaging device according to claim 1, wherein after correcting the nuclear magnetic resonance signals based on the phase offset distribution, in which the unwrap processing has already been judged as having been performed properly, the signal processing means reconstructs another image with regard to two different types of nuclear spins having different chemical shifts through the computation utilizing the generated nuclear magnetic resonance signals.

3. A magnetic resonance imaging method in which an inspection subject is laid in a space where a static magnetic field is formed, a high frequency magnetic field is irradiated onto the inspection subject while applying a gradient field to the static magnetic field, a nuclear magnetic resonance signal generated from the inspection subject in response to the irradiation is detected, an image of a predetermined portion of the inspection subject is reconstructed through a processing means based on the detected signal and the reconstructed image is displayed, said method comprising:
  a step of calculating first, second and third echo image data by making use of respectively plural first, second and third echo signals each having different echo time from the high frequency magnetic field irradiation to the nuclear magnetic resonance signal generation
  a step of forming a phase rotation amount distribution map representing a static magnetic field inhomogeneity from the first and third echo image data;
  a step of applying a first mask prepared based on the first echo image data to the phase rotation amount distribution map;
  a step of further applying a first loop mask to the phase rotation amount distribution map to which the first mask is applied;
  a step of performing a first unwrap processing with regard to respective pixel portions on the phase rotation amount distribution map to which the first mask and the first loop mask are not applied, forming a first unwrap processing state map based on a consistency of values of a same point obtained by the unwrap processing in at least two different directions of the first unwrap processing state map, in parallel with the first unwrap processing, and at the same time, judging properness of the first unwrap processing based on the prepared first unwrap processing state map;
  a step of forming an unwrap phase rotation amount distribution map by executing a function fitting with regard to pixel portions of non unwrap processing in the phase rotation amount distribution map which is judged as the unwrap processing is proper;
  a step of effecting a phase correction to the second echo image data based on the unwrap phase rotation amount distribution map;
  a step of calculating addition image data by adding the first echo image data and the phase corrected second echo image data;
  a step of calculating subtraction image data by subtracting the phase corrected second echo image data from the first echo image data; and
  a step of discriminating between one of the addition image data and the subtraction image data as water image data and the other as fat image data based on a ratio of pixel values determined for every pixel of the first and second echo image data,
  wherein when the first unwrap processing is judged improper in the first unwrap processing properness judgement step, performing:
  a step of applying a second mask, which is prepared, based on the second echo image data to the phase rotation amount distribution map;
  a step of performing a second unwrap processing on respective pixel portions in the phase rotation amount distribution map to which the second mask is not applied;
  a step of forming a second unwrap processing state map based on a consistency of values of a same point obtained by the unwrap processing in at least two different directions of the second unwrap processing state map, in parallel with the second unwrap processing;
  a step of judging properness of the second unwrap processing based on the prepared second unwrap processing state map; and
  a step of increasing one pixel by one pixel the loop maximum value of the first loop mask until the judgement changes from improper to proper.

4. A magnetic resonance imaging device which is provided with a magnetic field generation means which respectively generates a high frequency magnetic field and a gradient magnetic field in a space where a static magnetic field is formed, a signal processing means which detects a nuclear magnetic resonance signal generated from an inspection subject placed in the space and reconstructs an image therefrom and a display means which displays the reconstructed image, wherein the signal processing means performs, by making use of at least two nuclear magnetic resonance signals having different times TE from irradiation of the high frequency magnetic field signal to generation of the nuclear magnetic resonance signals, a computation determining a phase offset distribution between the generated nuclear magnetic resonance signals, and wherein the signal processing means performs an unwrap processing in which an unwrap processing state map is generated and a principal value of rotation caused in the computation determining the phase offset distribution is corrected, and at the same time, performs a judgement as to whether the unwrap processing is proper based on a consistency of values of a same point obtained by the unwrap processing in at least two different directions of the unwrap processing state map, and by making use of the nuclear magnetic resonance signals corrected based on the phase offset distribution judged as properly unwrap processed, reconstructs at least two original images, and further reconstructs two types of display images with regard to two different types of nuclear spins having different chemical shifts through comparison of these original images and subsequently performs an automatic discrimination of the obtained two display images from pixel values of the at least two original images and/or from pixel values of the two types of the display images.

5. A magnetic resonance imaging method in which an inspection subject is laid in a space where a static magnetic field is formed, a high frequency magnetic field is irradiated onto the inspection subject while applying a gradient field to the static magnetic field, a nuclear magnetic resonance signal generated from the inspection subject in response to the irradiation is detected, an image of a predetermined portion of the inspection subject is reconstructed based on the detected signal and the reconstructed image is displayed, comprising;
  a step of calculating first and second echo image data by making use of respectively plural first and second echo signals each having different echo time from the high frequency magnetic field irradiation to the nuclear magnetic resonance signal generation;
  a step of forming a phase rotation amount distribution map representing a static magnetic field inhomogeneity from the first and second echo image data;

a step of applying a first mask prepared based on the first echo image data to the phase rotation amount distribution map;

a step of further applying a first loop mask to the phase rotation amount distribution map to which the first mask is applied;

a step of performing a first unwrap processing with regard to respective pixel portions on the phase rotation amount distribution map to which the first mask and the first loop mask are not applied, forming a first unwrap processing state map based on a consistency of values of a same point obtained by the unwrap processing in at least two different directions of the first unwrap processing state map, in parallel with the first unwrap processing, and at the same time, judging properness of the first unwrap processing based on the prepared first unwrap processing state map;

a step of forming an unwrap phase rotation amount distribution map by executing a function fitting with regard to pixel portions of non unwrap processing in the phase rotation amount distribution map which is judged as the unwrap processing is proper;

a step of effecting a phase correction to the second echo image data based on the unwrap phase rotation amount distribution map;

a step of calculating addition image data by adding the first echo image data and the phase corrected second echo image data;

a step of calculating subtraction image data by subtracting the phase corrected second echo image data from the first echo image data; and a step of discriminating between one of the addition image data and the subtraction image data as water image data and the other as fat image data based on a ratio of pixel values determined for every pixel of the first and second echo image data.

6. A magnetic resonance imaging method according to claim 5, further comprising;

a step of discriminating between one of the addition image data and the subtraction image data as water image data and the other as fat image data based on respective pixel values of predetermined portions of the addition image data and the subtraction image data.

7. A magnetic resonance imaging method according to claim 5, further comprising when the first unwrap processing is judged improper in the first unwrap processing properness judgement step, performing:

a step of applying a second mask, which is prepared, based on the second echo image data to the phase rotation amount distribution map;

a step of performing a second unwrap processing on respective pixel portions in the phase rotation amount distribution map to which the second mask is not applied;

a step of forming a second unwrap processing state map based on a consistency of values of a same point obtained by the unwrap processing in at least two different directions of the second unwrap processing state map, in parallel with the second unwrap processing; and a step of judging properness of the second unwrap processing based on the prepared second unwrap processing state map.

8. A magnetic resonance imaging method according to claim 7, further comprising when the first unwrap processing is judged improper in the first unwrap processing properness judgement step, increasing one pixel by one pixel the loop maximum value of the first loop mask until the judgement changes from improper to proper.

9. A magnetic resonance imaging method according to claim 7, wherein the second mask is prepared based on a ratio (ec2/ec1) of the second echo image data with respect to the first echo image data, and further comprising:

a step of measuring an area of the first unwrap processing prior to the first unwrap processing step;

a step of measuring an area of the second unwrap processing prior to the second unwrap processing step;

a step of judging whether a ratio of the measured second unwrap processing area with respect to the measured first unwrap processing area is more than a predetermined value; and a step of reducing the mask threshold value of the second mask when the ratio is less than the predetermined value.

10. A magnetic resonance imaging method according to claim 5, further comprising:

representing the first and second echo image data in a matrix;

a step of reducing a matrix size of the first and second echo image data prior to the phase rotation amount map preparation step; and a step of restoring the matrix size of the first and second echo image data and the phase rotation amount map to the original one prior to effecting the phase correction to the second echo image data.

11. A magnetic resonance imaging method in which an inspection subject is laid in a space where a static magnetic field is formed, a high frequency magnetic field is irradiated onto the inspection subject while applying a gradient field to the static magnetic field, a nuclear magnetic resonance signal generated from the inspection subject in response to the irradiation is detected, an image of a predetermined portion of the inspection subject is reconstructed based on the detected signal and the reconstructed image is displayed, comprising:

a step of calculating first, second and third echo image data by making use of respectively plural first, second and third echo signals each having different echo time from the high frequency magnetic field irradiation to the nuclear magnetic resonance signal generation;

a step of forming a phase rotation amount distribution map representing a static magnetic field inhomogeneity from the first and third echo image data;

a step of applying a first mask prepared based on the first echo image data to the phase rotation amount distribution map;

a step of further applying a first loop mask to the phase rotation amount distribution map to which the first mask is applied;

a step of performing a first unwrap processing with regard to respective pixel portions on the phase rotation amount distribution map to which the first mask and the first loop mask are not applied, forming a first unwrap processing state map based on a consistency of values of a same point obtained by the unwrap processing in at least two different directions of the first unwrap processing state map, in parallel with the first unwrap processing, and at the same time, judging properness of the first unwrap processing based on the prepared first unwrap processing state map;

a step of forming an unwrap phase rotation amount distribution map by executing a function fitting with regard to pixel portions of non unwrap processing in the phase rotation amount distribution map which is judged as the unwrap processing is proper;

a step of effecting a phase correction to the second echo image data based on the unwrap phase rotation amount distribution map;

a step of calculating an addition image data by adding the first echo image data and the phase corrected second echo image data;

a step of calculating a subtraction image data by subtracting the phase corrected second echo image data from the first echo image data; and a step of discriminating between one of the addition image data and the subtraction image data as water image data and the other as fat image data based on a ratio of pixel values determined for every pixel of the first and second echo image data.

12. A magnetic resonance imaging device which is provided with a magnetic field generation means which respectively generates a high frequency magnetic field and a gradient magnetic field in a space where a static magnetic field is formed, a signal processing means which detects a nuclear magnetic resonance signal generated from an inspection subject placed in the space and reconstructs an image therefrom and a display means which displays the reconstructed image, wherein the signal processing means performs, by making use of at least two nuclear magnetic resonance signals having different times (TE) from irradiation of the high frequency magnetic field signal to generation of the nuclear magnetic resonance signals, a computation determining phase offset distribution between the generated nuclear magnetic resonance signals, a computation applying a mask to the determined phase offset distribution, and wherein the signal processing means performs an unwrap processing in which an unwrap processing state map is generated and a principal value of rotation caused in the computation determining the phase offset distribution is corrected, and at the same time, performs a judgment as to whether the unwrap processing is proper based on a consistency of values of a same point obtained by unwrap processing in at least two different directions of the unwrap processing state map, and then subsequently when the unwrap processing is improper, repeats the unwrap processing by changing the extent covered by the mask until the judgement changes from improper to proper.

13. A magnetic resonance imaging device which is provided with a magnetic field generation means which respectively generates a high frequency magnetic field and a gradient magnetic field in a space where a static magnetic field is formed, a signal processing means which detects a nuclear magnetic resonance signal generated from an inspection subject placed in the space and reconstructs an image therefrom and a display means which displays the reconstructed image, wherein the signal processing means performs, by making use of at least two nuclear magnetic resonance signals having different times (TE) from irradiation of the high frequency magnetic field signal to generation of the nuclear magnetic resonance signals, a computation determining a phase offset distribution between the generated nuclear magnetic resonance signals, and performs a computation applying a mask to the determined phase offset distribution, and wherein the signal processing means performs an unwrap processing in which an unwrap processing state map is generated and a principal value of rotation caused in the computation determining the phase offset distribution is corrected, and at the same time, performs a judgment as to whether the unwrap processing is proper based on a consistency of values of a same point obtained in the unwrap processing in at least two different directions of the unwrap processing state map, and by making use of the nuclear magnetic resonance signals corrected based on the phase offset distribution judged as properly unwrap processed, reconstructs at least two original images, and further reconstructs two types of display images with regard to two different types of nuclear spins having different chemical shifts through comparison of these original images and subsequently performs an automatic discrimination of the obtained two display images from pixel values of the at least two original images and/or from pixel values of the two types of the display images, and then subsequently when the unwrap processing is judged improper, repeats the unwrap processing by changing the extent covered by the mask until the judgment changes from improper to proper.

14. A magnetic resonance imaging method in which an inspection subject is laid in a space where a static magnetic field is formed, a high frequency magnetic field is irradiated onto the inspection subject while applying a gradient field to the static magnetic field, a nuclear magnetic resonance signal generated from the inspection subject in response to the irradiation is detected, an image of a predetermined portion of the inspection subject is reconstructed based on the detected signal and the reconstructed image is displayed, comprising:

step of calculating first and second echo image data by making use of respectively plural first and second echo signals each having different echo time from the high frequency magnetic field irradiation to the nuclear magnetic resonance signal generation a step of forming a phase rotation amount distribution map representing a static magnetic field inhomogeneity from the first and second echo image data;

a step of applying a mask to the phase rotation amount distribution map;

a step of performing an unwrap processing to respective pixel portions on the phase rotation amount distribution map to which the mask is not applied, forming an unwrap processing state map based on a consistency of values of a same point obtained by the wrap processing in at least two different directions of the unwrap processing state map, in parallel with the unwrap processing, and at the same time, judging whether the unwrap processing is proper based on the prepared unwrap processing state map;

a step of repeating the unwrap processing, subsequently when the unwrap processing is judged improper, while changing the extent to be covered by the mask until the judgment changes from improper to proper;

a step of determining through a function fitting a phase distribution of pixel portions of non unwrap processing in the phase rotation amount distribution map of which unwrap processing is judged proper;

a step of effecting a phase correction to the second echo image data based on the unwrap phase rotation amount distribution map; and a step of forming two types of images having different chemical shits through computation between the first echo image data and the phase corrected second echo image data.

15. A magnetic resonance imaging device which is provided with a magnetic field generation means which respectively generates a high frequency magnetic field and a gradient magnetic field in a space where a static magnetic field is formed, a signal processing means which detects a nuclear magnetic resonance signal generated from an inspection subject placed in the space and reconstructs an image therefrom and a display means which displays the reconstructed image, wherein the signal processing means, by making use of at least two nuclear magnetic resonance signals having different times (TE) from irradiation of the high frequency magnetic field signal to generation of the nuclear magnetic resonance signals, reconstructs at least two original images, and further reconstructs two types of display images with regard to two different types of nuclear spins having different chemical shifts through comparison of said at least two original images and subsequently performs an automatic discrimination of the obtained two display images from pixel values of the at least two original images and/or from pixel values of the two types of the display images, and wherein the signal processing means performs an unwrap processing in which an unwrap processing state map is generated and a principal value of rotation caused in the computation determining the phase offset distribution is corrected, and at the same time, performs a judgement as to whether the unwrap processing is proper based on a consistency of values of a same point obtained by the unwrap processing in at least two different directions of the unwrap processing state map.

16. A magnetic resonance imaging device according to claim according to claim 3, wherein as one of the display images another image representing a distribution of either one of nuclear spins among the two types of nuclear spins of different chemical shifts is discriminated.

17. A magnetic resonance imaging device according to claim 16, wherein as one of the display images a water image primarily representing a distribution of water protons is discriminated.

18. A magnetic resonance imaging device according to claim 16, wherein as one of the display images a fat image primarily representing a distribution of fat protons is discriminated.

19. A magnetic resonance imaging device according to claim 16, wherein the discrimination of the display images is performed by utilizing a ratio of pixel values of the at least two original images.

* * * * *